(12) United States Patent
Sun et al.

(10) Patent No.: US 9,792,403 B2
(45) Date of Patent: Oct. 17, 2017

(54) ANALYSIS OF GENETIC VARIANTS

(71) Applicants: James Xin Sun, Newton, MA (US); Roman Yelensky, Newton, MA (US)

(72) Inventors: James Xin Sun, Newton, MA (US); Roman Yelensky, Newton, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 0 days.

(21) Appl. No.: 14/274,525

(22) Filed: May 9, 2014

(65) Prior Publication Data

US 2014/0336996 A1 Nov. 13, 2014

Related U.S. Application Data

(60) Provisional application No. 61/939,936, filed on Feb. 14, 2014, provisional application No. 61/821,920, filed on May 10, 2013.

(51) Int. Cl.
*G01N 33/50* (2006.01)
*G06F 19/18* (2011.01)

(52) U.S. Cl.
CPC .................................. *G06F 19/18* (2013.01)

(58) Field of Classification Search
None
See application file for complete search history.

(56) References Cited

U.S. PATENT DOCUMENTS

| | | | |
|---|---|---|---|
| 2010/0028873 A1 | 2/2010 | Belouchi et al. | |
| 2011/0098193 A1* | 4/2011 | Kingsmore et al. | 506/9 |
| 2012/0095697 A1* | 4/2012 | Halpern et al. | 702/20 |
| 2012/0208706 A1 | 8/2012 | Downing et al. | |

FOREIGN PATENT DOCUMENTS

WO 2014183078 A1 11/2014

OTHER PUBLICATIONS

Van Loo et al. (Allele-Specific Copy number Analysis of Tumors, PNAS, Sep. 28, 2010, vol. 107, No. 39, pp. 16910-16915).*
Yelensky et al. Abstract. A statistical model for detecting gene amplification and homozygous deletion from targeted next-generation sequencing of clinical cancer specimens with significant stromal admixture. HiTSeq 2012: Conference on High Throughput Sequencing Methods and Applications on Jul. 13-14, 2012, in Long Beach, CA, USA.
Yelensky et al. Presentation. A statistical model for detecting gene amplification and homozygous deletion from targeted next-generation sequencing of clinical cancer specimens with significant stromal admixture. HiTSeq 2012: Conference on High Throughput Sequencing Methods and Applications on Jul. 13-14, 2012, in Long Beach, CA, USA.
Sun et al. Abstract. A computational method for somatic vs. germline variant status determination from targeted NGS of clinical cancer specimens without a matched normal control. HiTSeq 2013: Conference on High Throughput Sequencing Methods and Applications on Jul. 19-20, 2013, Berlin, Germany.
Sun et al. Poster presentation. A computational method for somatic vs germ-line variant status determination from targeted next-generation sequencing of clinical cancer specimens without a matched normal control. 15th Annual Advances in Genome Biology & Technology (AGBT) Meeting, Feb. 12-15, 2014, Marco Island, Florida, USA.
Sun et al. Abstract. A computational method for somatic versus germline variant status determination from targeted next-generation sequencing of clinical cancer specimens without a matched normal control. American Association of Cancer Research (AACR) 105th Annual Meeting. Apr. 5-9, 2014, San Diego, USA. Abstract bodies made available online on Mar. 5, 2014.
Sun et al. Poster. A computational method for somatic versus germline variant status determination from targeted next-generation sequencing of clinical cancer specimens without a matched normal control. American Association of Cancer Research (AACR) 105th Annual Meeting. Apr. 5-9, 2014, San Diego, USA.
Carter, SL et al., "Absolute Quantification of Somatic DNA Alterations in Human Cancer", Nat Biotechnol., vol. 30, No. 5, pp. 413-421, May 2012.
International Search Report and Written Opinion dated Oct. 7, 2014 from International Application No. PCT/US14/37569.
Van Loo, P. et al., "Allele-Specific Copy Number Analysis of Tumors", Proc Natl Acad Sci, vol. 107, No. 39, pp. 16910-16915, Sep. 28, 2010.
Jones, S. et al., "Personalized Genomic Analyses for Cancer Mutation Discovery and Interpretation", Science Translation Medicine, vol. 7, Issue 283, pp. 1-10, Apr. 15, 2015.
Frampton, G.M. et al., "Development and Validation of a Clinical Cancer Genomic Profiling Test Based on Massively Parallel DNA Sequencing", Nature Biotechnology, Oct. 20, 2013, pp. 1-11.
Greenman, C.D. et al., "PICNIC: An Algorithm to Predict Absolute Allelic Copy Number Variation with Microarray Cancer Data", Biostatistics, 2010, 11, 1, pp. 164-175.
Kallioniemi, A. et al., "Comparative Genomic Hybridization for Molecular Cytogenetic Analysis of Solid Tumors", Science, vol. 258, Oct. 30, 1992, pp. 818-821.
Yau, Christopher, "OncoSNP-SEQ: A Statistical Approach for the Identification of Somatic Copy Number Alterations from Next-Generation Sequencing of Cancer Genomes", Bioinformatics, vol. 29, No. 19, 2013, pp. 2482-2484.
Extended European Search Report for European Application No. EP 14795352.5 dated Mar. 20, 2017.

* cited by examiner

*Primary Examiner* — Jason Sims
(74) *Attorney, Agent, or Firm* — Lando & Anastasi, LLP

(57) ABSTRACT

Methods and systems for analyzing genetic variants are disclosed.

22 Claims, 10 Drawing Sheets

FIG. 7

| copy number | LOH status | status of variant | sample purity (p) | | | | | | | | | | |
|---|---|---|---|---|---|---|---|---|---|---|---|---|---|
| | | | 0 | 10 | 20 | 30 | 40 | 50 | 60 | 70 | 80 | 90 | 100 |
| C=1 | LOH | M=0 germline | 50 | 47 | 44 | 41 | 38 | 33 | 29 | 23 | 17 | 9 | 0 |
| | | M=1 somatic | 0 | 5 | 11 | 18 | 25 | 33 | 43 | 54 | 67 | 82 | 100 |
| | | M=1 germline | 50 | 53 | 56 | 59 | 63 | 67 | 71 | 77 | 83 | 91 | 100 |
| C=2 | LOH | M=0 germline | 50 | 45 | 40 | 35 | 30 | 25 | 20 | 15 | 10 | 5 | 0 |
| | | M=2 somatic | 0 | 10 | 20 | 30 | 40 | 50 | 60 | 70 | 80 | 90 | 100 |
| | | M=2 germline | 50 | 55 | 60 | 65 | 70 | 75 | 80 | 85 | 90 | 95 | 100 |
| | het | M=1 somatic | 0 | 5 | 10 | 15 | 20 | 25 | 30 | 35 | 40 | 45 | 50 |
| | | M=1 germline | 50 | 50 | 50 | 50 | 50 | 50 | 50 | 50 | 50 | 50 | 50 |

FIG. 8

ANALYSIS OF GENETIC VARIANTS

CROSS REFERENCE TO RELATED APPLICATIONS

This application claims the benefit of U.S. Provisional Application No. 61/821,920, filed May 10, 2013 and U.S. Provisional Application No. 61/939,936, filed Feb. 14, 2014, the contents of which are hereby incorporated by reference in their entirety.

FIELD OF INVENTION

The disclosure relates to the analysis of genetic variants.

BACKGROUND

Typically, cancer tissues are characterized by genetic lesions which are, at least in part, responsible for the occurrence or phenotype of the disorder. Many cancers are characterized by one or more genetic aberrations, including gene copy number changes, somatic and germline mutations. The need still exists for analyzing genetic variants associated with cancer.

SUMMARY

The disclosure features, inter alia, methods and systems for analyzing or characterizing variants in a tumor, e.g., generating a characterization model for a variant (e.g., a mutation) in a tissue (e.g., a tumor or tumor sample) from a subject (e.g., a human subject, e.g., a cancer patient). Embodiments described herein allow for the analysis without the need for analyzing non-tumor tissue from the subject. For example, the methods described herein can be used in genomic testing that includes variants, e.g., novel variants, whose somatic status is unknown or unclear. The characterization can include assessment or indication of zygosity and/or variant type, e.g., as somatic or germline. The assessment has numerous uses including: obtaining an understanding of the genetic lesions in a cancer; selecting a treatment modality, e.g., in response to the analysis; staging, diagnosing, or prognosing a subject, e.g., in response to the analysis; developing novel therapeutic agents; the discovery and use of existing therapeutic agents for disorders not previously treated with that therapeutic agent; selection of subjects for experimental trials; understanding mechanisms of tumor characteristics, e.g., tumor metabolism, growth, invasiveness, resistance or susceptibility to therapy; selection or discovery of treatment regimes, e.g., drug combinations, e.g., for simultaneous use or for sequential use, e.g., as early or subsequent line of treatment; and assembling databases of tumor characteristics. The systems and methods disclosed herein are also useful for developing compositions, assays, kits, devices, systems, and methods for treating cancer. The systems and methods disclosed herein can inform clinical decision making and expand treatment choices for cancer patients.

In one aspect, the disclosure provides, a system for generating a characterization model (including, e.g., variant type and/or zygosity) for a variant (e.g., a mutation) in a tissue or sample, e.g., a tumor, or tumor sample, from a subject, e.g., a human subject, e.g., a cancer patient. The system comprises:

at least one processor operatively connected to a memory, the at least one processor when executing is configured to:

a) acquire:
  i) a sequence coverage input (SCI), which comprises, for each of a plurality of selected subgenomic intervals (e.g., exons) a value for sequence coverage at the selected subgenomic intervals (including, e.g., a normalized sequence coverage value);
  ii) an SNP allele frequency input (SAFI), which comprises, for each of a plurality of selected germline SNPs, a value for the allele frequency, in the tissue or sample, e.g., tumor sample;
  iii) a variant allele frequency input (VAFI), which comprises the allele frequency for said variant, e.g., mutation, in the tissue or sample, e.g., tumor sample;
b) acquire values, determined as a function of SCI and SAFI, for:
  a genomic segment total copy number (C), for each of a plurality of genomic segments;
  a genomic segment minor allele copy number (M), for each of a plurality of genomic segments; and
  sample purity (p); and
c) calculate one or both, of:
  i) a value for variant type, e.g., mutation type, e.g., g, which is indicative of the variant being somatic, germline, subclonal somatic, or not-distinguishable, wherein the at least one processor when executing is configured calculate the value for variant type, e.g., mutation type, as a function of VAFI, p, C, and M;
  ii) an indication of the zygosity (e.g., homozygous, heterozygous, and absent) of the variant, e.g., mutation, in the tissue or sample, e.g., tumor sample, as function of C and M.

In an embodiment, the system is configured such that the analysis can be performed without the need for analyzing non-tumor tissue from the subject.

In an embodiment, the analysis is performed without analyzing non-tumor tissue from the subject, e.g., non-tumor tissue from the same subject is not sequenced.

In an embodiment, the system is configured to determine for at least one of the tumor sample, the selected subgenomic intervals, and the selected germline SNPs that the variant type, e.g., mutation type, cannot be determined for analyzed values.

In an embodiment, at least one processor when executing acquires the SCI calculated as a function (e.g., the log of the ratio) of the number of reads for a subgenomic interval and the number or reads for a control (e.g., a process-matched control).

In an embodiment, at least one processor when executing is configured to calculate SCI as a function (e.g., the log of the ratio) of the number of reads for a subgenomic interval and the number or reads for a control (e.g., a process-matched control).

In an embodiment, the at least one processor when executing is configured to validate a minimum number of subgenomic intervals have been selected or analyzed.

In an embodiment, the at least one processor when executing is configured to acquire the SCI from values calculated against at least 10, 25, 50, 100, 150, 200, 250, 300, 350, 400, 450, 500, 1,000, 2,000, 3,000, or 4,000, subgenomic intervals (e.g., exons).

In an embodiment, the at least one processor when executing is configured to calculate the SCI against at least 10, 25, 50, 100, 150, 200, 250, 300, 350, 400, 450, 500, 1,000, 2,000, 3,000, or 4,000, subgenomic intervals (e.g., exons).

In an embodiment, the SCI comprises a plurality of respective values (e.g., log r values) for a plurality of subgenomic intervals (e.g., exons) from at least 10, 25, 50, 100, 150, 200, 250, 300, 350, 400, 450, 500, 1,000, 2,000, 3,000, or 4,000, genes.

In an embodiment, at least one, a plurality, or substantially all of the values comprised in the SCI are corrected for correlation with GC content.

In an embodiment, at least one processor when executing is configured to validate a minimum number of a plurality of germline SNPs have been selected or analyzed.

In an embodiment, the minimum number of germline SNPs comprises at least 10, 25, 50, 100, 150, 200, 250, 300, 350, 400, 450, 500, 1,000, 2,000, 3,000, 4,000, 5000, 6000, 7000, 8000, 9000, 10,000, or 15,000 germline SNPs.

In an embodiment, the SAFI is based, at least in part, on a minor allele frequency in the tumor sample.

In an embodiment, the at least one processor when executing is configured to calculate, or acquire, SAFI based, at least in part, on a minor allele frequency in the tumor sample.

In an embodiment, the SAFI is based, at least in part, on an alternative allele frequency (e.g., an allele frequency other than a standard allele in a human genome reference database).

In an embodiment, the at least one processor when executing is configured to calculate, or acquire, SAFI based, at least in part, on an alternative allele frequency (e.g., an allele frequency other than a standard allele in a human genome reference database).

In an embodiment, the at least one processor when executing is configured to access values of C, M, and p calculated from fitting a genome-wide copy number model to the SCI and the SAFI.

In an embodiment, the at least one processor when executing is configured to calculate C, M, and p.

In an embodiment, the at least one processor when executing generates a best fit between the genome-wide copy number model and the SCI and the SAFI to calculate C, M, and p.

In an embodiment, values of C, M, and p fit a plurality of genome-wide copy number model inputs of the SCI and the SAFI.

In an embodiment, the at least one processor when executing is configured to access or calculate one or more genome-wide copy number models.

In an embodiment, the at least one processor when executing is configured to determine a confidence value for each of the plurality of genome-wide copy number models based on a determined fit to the SCI and the SAFI.

In an embodiment, the at least one processor when executing is configured to calculate C, M, and p, responsive to contributions from each of the plurality of genome-wide copy models.

In an embodiment, the contributions are determined according to a confidence level for each of the plurality of genome-wide copy models (including, e.g., confidence levels reflective of a degree of fit).

In an embodiment, a genomic segment comprises a plurality of subgenomic intervals, e.g., exons, e.g., subgenomic intervals, e.g., exons, which have been assigned a SCI value.

In an embodiment, the system is configured to calculate and/or assign SCI values to a plurality of subgenomic intervals.

In an embodiment, the at least one processor when executing is configured to require a minimum number of subgenomic intervals for analysis of a genomic segment.

In an embodiment, a genomic segment comprises at least 10, 20, 30, 40, 50, 60, 70, 80, 90, 100, 125, 150, 175, 200, 225, 250, 275, 300, 400, or 500 subgenomic intervals, e.g., exons.

In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100, subgenomic intervals (e.g., exons).

In an embodiment, a genomic segment comprises between 100 and 10,000, 100 and 5,000, 100 and 4,000, 100 and 3,000, 100 and 2,000, or 100 and 1,000, subgenomic intervals (e.g., exons).

In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100 genomic SNPs, which have been assigned a SAFI value.

In an embodiment, a genomic segment comprises between 100 and 10,000, 100 and 5,000, 100 and 4,000, 100 and 3,000, 100 and 2,000, or 100 and 1,000, genomic SNPs which have been assigned a SAFI value.

In an embodiment, the at least one processor when executing is configured to validate each of a plurality of genomic segments with values having one or both of:
  a measure of normalized sequence coverage, e.g., log r, that differ by no more than a preselected amount, e.g., the values for log 2 r for subgenomic intervals, e.g., exons, within the boundaries of the genomic segment differ by no more than a reference value, or are substantially constant; and
  SNP allele frequencies for germline SNPs that differ by no more than a preselected amount, e.g., the values for germline SNP allele frequencies for subgenomic intervals, e.g., exons, within the boundaries of the genomic segment differ by no more than a reference value, or are substantially constant.

In an embodiment, the at least one processor when executing is configured to require the number of subgenomic intervals (e.g., exons) that are contained in, or are combined to form, a genomic segment is at least 2, 5, 10, 15, 20, 50, or 100 times the number of genomic segments.

In an embodiment, the at least one processor when executing is configured to require the number of subgenomic intervals, e.g., exons, is at least 3, 4, 5, 6, 7, 8, 9, 10, 11, 12, 13, 14, or 15 times the number of genomic segments.

In an embodiment, the at least one processor when executing is configured to define a boundary for a genomic segment (e.g., automatically define boundary, accept user input on the boundary, generate relative boundary from user provided inputs, display a user interface for defining genomic segment boundary, display suggested boundary, etc.).

In an embodiment, the at least one processor when executing is configured to assemble sequences of subgenomic intervals (e.g., exons) into genetic segments (including, e.g., user identified subgenomic intervals, system identified subgenomic intervals, candidate subgenomic intervals, user confirmed candidate subgenomic intervals).

In an embodiment, the at least one processor when executing is configured to segment a genomic sequence into subgenomic intervals of equal copy number (e.g., according to circular binary segmentation (CBS) algorithms, an HMM based method, a Wavelet based method, or a Cluster along Chromosomes method).

In an embodiment, the at least one processor when executing is configured to assemble subgenomic intervals into genomic segments of equal copy number (e.g., according to circular binary segmentation (CBS) algorithms, an HMM based method, a Wavelet based method, or a Cluster along Chromosomes method).

In an embodiment, the at least one processor when executing is configured to assemble sequences for subgenomic intervals according to a method described herein (e.g., circular binary segmentation function (CBS) an HMM based method, a Wavelet based method, or a Cluster along Chromosomes method).

In an embodiment, the at least one processor when executing is configured to fit the genome-wide copy number model to the SCI according to calculation of:

$$\log Ratio_i = \log_2 \frac{pC_i + 2(1-p)}{p\psi + 2(1-p)},$$

where $\psi$ is tumor ploidy.

In an embodiment, the at least one processor is configured to determined $\psi=(\Sigma_i l_i C_i)/\Sigma_i l_i)$, wherein $l_i$ is determined based at least in part on the length of a genomic segment being analyzed.

In an embodiment, the at least one processor when executing is configured to fit the genome-wide copy number model to the SAFI according to calculation of:

$$AF = \frac{pM + 1(1-p)}{pC + 2(1-p)},$$

where AF is allele frequency.

In an embodiment, the at least one processor when executing is configured to fit the genome-wide copy number model according to execution of Gibbs sampling.

In an embodiment, the at least one processor when executing is configured to fit the genome-wide copy number model by determining a best fit model from a fitting algorithm (e.g., Markov chain Monte Carlo (MCMC) algorithm, e.g., ASCAT (Allele-Specific Copy Number Analysis of Tumors), OncoSNP, or PICNIC (Predicting Integral Copy Numbers In Cancer).

In an embodiment, the fitting comprises using Metropolis-Hastings MCMC.

In an embodiment, the fitting comprises using a non-Bayesian approach (e.g., a frequentist approach, e.g., using least squares fitting).

In an embodiment, the at least one processor when executing is configured to determine g by calculating a fit of values for VAFI, p, C, and M to a model for somatic/germline status.

In an embodiment, the at least one processor when executing is configured to determine g by solving for g in $$AF = \frac{pM + g(1-p)}{pC + 2(1-p)}.$$

In an embodiment, the at least one processor when executing is configured to classify a type of variant responsive to a calculated value of g.

In an embodiment, the at least one processor when executing is configured to classify the type of variant based on at least one of:

for the g value sufficiently close to 0, classify the variant as a somatic variant; (e.g., with a predetermined distance from 0)

for the g value approximately equal to 1 (e.g., with a predetermined distance from 1), or higher, classify the variant as a germline variant; and for the g value between 0 and 1, evaluate the g value to determine that it is not close to either the somatic classification value or the germline classification value (e.g., 0.4 to 0.6), and classify the variant as indistinguishable; and for the g value less than 0, classify the variant as a subclonal somatic variant.

In an embodiment, the at least one processor when executing is configured to define an indistinguishable range of values for g responsive to local evaluation of the genomic segment calculations.

In an embodiment, the at least one processor when executing is configured to define the indistinguishable range of values based on a confidence level associated with calculated values, wherein the greater the confidence level the smaller the range of values of g defining the indistinguishable range, and wherein the smaller the confidence level the greater the range of values of g defining the indistinguishable range of values.

In an embodiment, the at least one processor when executing is configured to classify a zygosity of the variant responsive to a calculated value indicating heterozygosity.

In an embodiment, the at least one processor when executing is configured to determine the sample purity (p) as a global purity value (e.g., is the same for all genomic segments).

In an embodiment, the at least one processor when executing is configured to determine the value of g according to:

$$AF = \frac{pM + g(1-p)}{pC + 2(1-p)},$$

where AF is allele frequency (e.g., the variant is a germline polymorphism if g=1 and the variant is a somatic mutation if g=0).

In an embodiment, the at least one processor when executing is configured to determine that a g value is approximately equal to 1 and classify the variant as a germline polymorphism.

In an embodiment, the at least one processor when executing is configured to determine that a g value is approximately equal to 1 (e.g., greater than 0.6) and classify the variant as a germline polymorphism.

In an embodiment, the at least one processor when executing is configured to determine that a g value is approximately equal to 0 (e.g., less than 0.4) and classify the variant as a somatic mutation.

In an embodiment, the at least one processor when executing is configured to determine that a g value is approximately equal to a classification value (e.g., g is approximately 1 or 0) responsive to a degree of statistical confidence in the calculations.

In an embodiment, the at least one processor when executing is configured to determine that a g value is significantly less than 0, and classify the variant as a subclonal somatic variant.

In an embodiment, the at least one processor when executing is configured to determine the value of g according to:

$$AF = \frac{pM' + g(1-p)}{pC + 2(1-p)},$$

where AF is allele frequency, and M'=C−M (e.g., when M is a non-minor allele frequency) (e.g., the variant is a germline polymorphism if g=1 and the variant is a somatic mutation if g=0).

In an embodiment, the somatic/germline status is determined when the sample purity is below, for example, about 40% (e.g., between about 10% and 30% (e.g., between about 10% and 20% or between about 20% and 30%)).

In an embodiment, the at least one processor when executing is configured to validate purity values.

In an embodiment, the at least one processor when executing is configured to define a confidence level for a calculation based on the sample purity value.

In an embodiment, the at least one processor when executing is configured to increase a confidence level for a determination of variant type based on a low purity (e.g., 10–30%), and/or decrease a confidence level for a determination of zygosity based on a low purity (e.g., 10–30%), and/or increase a confidence level for a determination of zygosity based on a high purity (e.g., >90%), and/or decrease a confidence level for a determination of variant type based on a high purity (e.g., >90%).

In an embodiment, the at least one processor when executing is configured to classify the variant according to:
a value of M equal to 0 not equal to C indicates an absence of the variant, e.g., mutation, e.g., not existent in the tumor;
a non-zero value of M equal to C indicates a homozygosity of the variant, e.g., mutation, e.g., with loss of heterozygosity (LOH);
a value of M equal to 0 equal to C indicates a homozygous deletion of the variant, e.g., mutation, e.g., not existent in the tumor; and
a non-zero value of M not equal to C indicates a heterozygosity of the variant, e.g., mutation.

In an embodiment, the at least one processor when executing is configured to determine an indication of zygosity for said variant (e.g., mutation).

In an embodiment, the at least one processor when executing is configured to determine the indication of zygosity for said variant is homozygous when M=C≠0 (including, for example, M is approximately equal to C), e.g., with LOH.

In an embodiment, the at least one processor when executing is configured to determine the indication of zygosity for said variant is homozygously deleted when M=C=0 (including, for example, M is approximately equal to C).

In an embodiment, the at least one processor when executing is configured to determine the indication of zygosity for said variant is heterozygous when 0<M<C.

In an embodiment, the at least one processor when executing is configured to determine the indication of zygosity for said variant is absent from the tumor when M=0 and C≠0 (including, for example, M is approximately equal to 0).

In an embodiment, the at least one processor when executing is configured to require the sample purity is greater than about 80%, e.g., between about 90% and 100%, e.g., between about 90% and 95%, or between about 95% and 100%, when determining the zygosity.

In an embodiment, the at least one processor when executing in configured to process-match control values using values obtained where the control is a sample of euploid (e.g., diploid) tissue from a subject other than the subject from which the tumor sample is from, or a sample of mixed euploid (e.g., diploid) tissues from one or more (e.g., at least 2, 3, 4, or 5) subjects other than the subject from which the tumor sample is from.

In an embodiment, the at least one processor when executing is configured to sequence each of the selected subgenomic intervals and each of the selected germline SNPs, e.g., by next generation sequencing (NGS).

In an embodiment, the at least one processor when executing is configured to determine sequence coverage prior to normalization is at least about 10×, 20×, 30×, 50×, 100×, 250×, 500×, 750×, or 1000× the depth of the sequencing.

In an embodiment, the subject has received an anti-cancer therapy.

In an embodiment, the subject has received an anti-cancer therapy and is resistant to the therapy or exhibits disease progression.

In an embodiment, the subject has received an anti-cancer therapy which is selected from: a therapeutic agent that has been approved by the FDA, EMEA, or other regulatory agency; or a therapeutic agent that has been not been approved by the FDA, EMEA, or other regulatory agency.

In an embodiment, the subject has received an anti-cancer therapy in the course of a clinical trial, e.g., a Phase I, Phase II, or Phase III clinical trial (or in an ex-US equivalent of such a trial).

In an embodiment, the variant is positively associated with the type of tumor present in the subject, e.g., with occurrence of, or resistance to treatment.

In an embodiment, the variant is not positively associated with the type of tumor present in the subject.

In an embodiment, the variant is positively associated with a tumor other than the type of tumor present in the subject.

In an embodiment, the variant is a variant that is not positively associated with the type of tumor present in the subject.

In an embodiment, the system is configured to memorialize, e.g., in a database, e.g., a machine readable database, provide a report containing, or transmit, a descriptor for one or more of: the presence, absence, or frequency, of other mutations in the tumor, e.g., other mutations associated with the tumor type in the sample, other mutations not associated with the tumor type in the sample, or other mutations associated with a tumor other than the tumor type in the sample; the characterization of the variant; the allele or gene; or the tumor type, e.g., the name of the type of tumor, whether the tumor is primary or secondary; a subject characteristic; or therapeutic alternatives, recommendations, or choices.

In an embodiment, a descriptor relating to the characterization of the variant comprises a descriptor for zygosity or germline vs. somatic status.

In an embodiment, a descriptor relating to a subject characteristic comprises a descriptor for one or more of: the subject's identity; one or more of the subject's, age, gender, weight, or other similar characteristic, occupation; the subject's medical history, e.g., occurrence of the tumor or of other disorders; the subject's family medical history, e.g., relatives who share or do not share the variant; or the subject's prior treatment history, e.g., the treatment received, response to a previously administered anti-cancer therapy, e.g., disease resistance, responsiveness, or progression.

In an embodiment, the system is in communication with a system that provides one or more of: sequencing data, e.g., raw sequencing data; or sequence analysis.

In an embodiment, the system can further provide one or more of: sequencing data, e.g., raw sequencing data; or sequence analysis.

In an embodiment, the at least one processor when executing is configured to generate a user interface.

In an embodiment, the user interface is configured to accept as input any one or more of:
- a sequence coverage input (SCI), which comprises, for each of a plurality of selected subgenomic intervals, e.g., exons, a value for sequence coverage at the selected subgenomic intervals (including, e.g., a normalized sequence coverage value);
- an SNP allele frequency input (SAFI), which comprises, for each of a plurality of selected germline SNPs, a value for the allele frequency, in the tumor sample;
- a variant allele frequency input (VAFI), which comprises the allele frequency for said variant, e.g., mutation, in the tumor sample;
- a genomic segment total copy number (C), for each of a plurality of genomic segments;
- a genomic segment minor allele copy number (M), for each of a plurality of genomic segments; and
- sample purity (p).

In an embodiment, responsive to the user interface input, e.g., for one or more (e.g., 2, 3, 4, 5 or all) of SCI, SAFI, VAFI, C, M, or p, the system generates a characterization model, e.g., a characterization model for a variant as described herein.

In an embodiment, the user interface is configured to display subgenomic intervals or a value calculated therefrom.

In an embodiment, the user interface is configured to accept user input selecting a plurality of subgenomic intervals on which to evaluate the tumor sample from the subject.

In an embodiment, the user interface is configured to display germline SNPs for the tumor sample.

In an embodiment, the user interface is configured to accept user input selecting a plurality of germline SNPs on which to evaluate the tumor sample.

In an embodiment, the user interface is configured to accept user defined confidence level for calculated values (e.g., calculated value described above).

In an embodiment, the user interface is configured to accept user input to define a boundary for a genomic segment.

In an embodiment, the user interface is configured to display a system generated genomic segment boundary for acceptance or modification by a user.

In another aspect, the disclosure features, a method of characterizing a variant, e.g., a mutation, in a tissue or sample, e.g., a tumor, or tumor sample, from a subject, e.g., a human, e.g., a cancer patient, comprising:

a) acquiring:
  i) a sequence coverage input (SCI), which comprises, for each of a plurality of selected subgenomic intervals, e.g., exons, a value for normalized sequence coverage at the selected subgenomic intervals;
  ii) an SNP allele frequency input (SAFI), which comprises, for each of a plurality of selected germline SNPs, a value for the allele frequency, in the tumor or sample, e.g., tumor sample;
  iii) a variant allele frequency input (VAFI), which comprises the allele frequency for said variant, e.g., mutation, in the tumor or sample, e.g., tumor sample;

b) acquiring values, as a function of SCI and SAFI, for:
  C, for each of a plurality of genomic segments, wherein C is a genomic segment total copy number;
  M, for each of a plurality of genomic segments, wherein M is a genomic segment minor allele copy number; and
  p, wherein p is sample purity; and c) acquiring one or both of:
  i) a value for variant type, e.g. mutation type, e.g., g, which is indicative of the variant, e.g., a mutation, being somatic, a subclonal somatic variant, germline, or not-distinguishable, and is a function of VAFI, p, C, and M;
  ii) an indication of the zygosity of the variant, e.g., mutation, in the tumor or sample, e.g., tumor sample, as function of C and M.

In an embodiment the analysis can be performed without the need for analyzing non-tumor tissue from the subject.

In an embodiment, the analysis is performed without analyzing non-tumor tissue from the subject, e.g., non-tumor tissue from the same subject is not sequenced.

In an embodiment, the SCI comprises values that are a function, e.g., the log of the ratio, of the number of reads for a subgenomic interval, e.g., from the sample, and the number or reads for a control, e.g., a process-matched control.

In an embodiment, the SCI comprises values, e.g., log r values, for at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subgenomic intervals, e.g., exons.

In an embodiment, the SCI comprises values, e.g., log r values, for at least 100 subgenomic intervals, e.g., exons.

In an embodiment, the SCI comprises values, e.g., log r values, for 1,000 to 10,000, 2,000 to 9,000, 3,000 to 8,000, 3,000 to 7,000, 3,000 to 6,000, or 4,000 to 5,000, subgenomic intervals, e.g., exons.

In an embodiment, the SCI comprises values, e.g., log r values, for subgenomic intervals, e.g., exons, from at least 10, 25, 50, 100, 150, 200, 250, 300, 350, 400, 450, 500, 1,000, 2,000, 3,000, or 4,000, genes.

In an embodiment, at least one, a plurality, or substantially all of the values comprised in the SCI are corrected for correlation with GC content.

In an embodiment, a subgenomic interval, e.g., an exon, from the sample has at least 10, 20, 30, 40, 50, 100, 150, 200, 250, 300, 350, 400, 450, 500, 600, 700, 800, 900, or 1,000 reads.

In an embodiment, a plurality, e.g., at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subgenomic intervals, e.g., exons, from the sample has a predetermined number of reads.

In an embodiment, the predetermined number of reads is at least 10, 20, 30, 40, 50, 100, 150, 200, 250, 300, 350, 400, 450, 500, 600, 700, 800, 900, or 1,000.

In an embodiment, the plurality of germline SNPs comprise at least 10, 25, 50, 100, 150, 200, 250, 300, 350, 400, 450, 500, 1,000, 2,000, 3,000, 4,000, 5000, 6000, 7000, 8000, 9000, 10,000, or 15,000 germline SNPs.

In an embodiment, the plurality of germline SNPs comprise at least 100 germline SNPs.

In an embodiment, the plurality of germline SNPs comprises 500 to 5,000, 1,000 to 4,000, or 2,000 to 3,000 germline SNPs.

In an embodiment, the allele frequency is a minor allele frequency.

In an embodiment, the allele frequency is an alternative allele, e.g., an allele other than a standard allele in a human genome reference database.

In an embodiment, the method comprises characterizing a plurality of variants, e.g., mutants, in the tumor sample.

In an embodiment, the method comprises characterizing at least 2, 3, 4, 5, 6, 7, 8 9, 10, 25, 50, 100, 150, 200, 250, 300, 350, 400, 450, or 500 variants, e.g., mutants.

In an embodiment, the method comprises characterizing variants, e.g., mutants, in at least 2, 3, 4, 5, 6, 7, 8 9, 10, 25, 50, 100, 150, 200, 250, 300, 350, 400, 450, or 500 different genes.

In an embodiment, the method comprises acquiring a VAFI for at least 2, 3, 4, 5, 6, 7, 8 9, 10, 25, 50, 100, 150, 200, 250, 300, 350, 400, 450, or 500 variants, e.g., mutants.

In an embodiment, the method comprises performing one, two or all, of steps a), b), and c) for at least 2, 3, 4, 5, 6, 7, 8 9, 10, 25, 50, 100, 150, 200, 250, 300, 350, 400, 450, or 500 variants, e.g., mutants.

In an embodiment, values of C, M, and p are, have, or can be obtained by, fitting a genome-wide copy number model to one or both of the SCI and the SAFI.

In an embodiment, values of C, M, and p fit a plurality of genome-wide copy number model inputs of the SCI and the SAFI.

In an embodiment, a genomic segment comprises a plurality of subgenomic intervals, e.g., exons, e.g., subgenomic intervals which have been assigned a SCI value.

In an embodiment, a genomic segment comprises at least 10, 20, 30, 40, 50, 60, 70, 80, 90, 100, 125, 150, 175, 200, 225, 250, 275, 300, 400, or 500 subgenomic intervals, e.g., exons.

In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100, subgenomic intervals, e.g., exons.

In an embodiment, a genomic segment comprises between 100 and 10,000, 100 and 5,000, 100 and 4,000, 100 and 3,000, 100 and 2,000, or 100 and 1,000, subgenomic intervals, e.g., exons.

In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100 genomic SNPs, which have been assigned a SAFI value.

In an embodiment, a genomic segment comprises between 100 and 10,000, 100 and 5,000, 100 and 4,000, 100 and 3,000, 100 and 2,000, or 100 and 1,000, genomic SNPs which have been assigned a SAFI value.

In an embodiment, each of a plurality of genomic segments are characterized by having one or both of:
 a measure of normalized sequence coverage, e.g., log r, that differ by no more than a preselected amount, e.g., the values for $\log_2 r$ for subgenomic intervals, e.g., exons, within the boundaries of the genomic segment differ by no more than a reference value, or are substantially constant; and
 SNP allele frequencies for germline SNPs that differ by no more than a preselected amount, e.g., the values for germline SNP allele frequencies for subgenomic intervals, e.g., exons, within the boundaries of the genomic segment differ by no more than a reference value, or are substantially constant.

In an embodiment, the number of subgenomic intervals, e.g., exons, that are contained in, or are combined to form, a genomic segment is at least 2, 5, 10, 15, 20, 50, or 100 times the number of genomic segments.

In an embodiment, the number of subgenomic intervals, e.g., exons, is at least 3, 4, 5, 6, 7, 8, 9, 10, 11, 12, 13, 14, or 15 times the number of genomic segments.

In an embodiment, a boundary for a genomic segment is provided.

In an embodiment, the method comprises assembling sequences for subgenomic intervals, e.g., exons, into genetic segments.

In an embodiment, the method comprises assembling sequences for subgenomic intervals, with a method described herein, e.g., a method comprising a circular binary segmentation (CBS), an HMM based method, a Wavelet based method, or a Cluster along Chromosomes method.

In an embodiment, fitting the genome-wide copy number model to the SCI comprises using the equation of:

$$\log Ratio_i = \log_2 \frac{pC_i + 2(1-p)}{p\psi + 2(1-p)},$$

where $\psi$ is tumor ploidy.

In an embodiment, $\psi = (\Sigma_i l_i C_i)/\Sigma_i l_i$, let $l_i$ be the length of a genomic segment.

In an embodiment, fitting the genome-wide copy number model to the SAFI comprises using the equation of:

$$AF = \frac{pM + 1(1-p)}{pC + 2(1-p)},$$

where AF is allele frequency.

In an embodiment, the fitting comprises using Gibbs sampling.

In an embodiment, fitting comprises using e.g., Markov chain Monte Carlo (MCMC) algorithm, e.g., ASCAT (Allele-Specific Copy Number Analysis of Tumors), OncoSNP, or PICNIC (Predicting Integral Copy Numbers In Cancer).

In an embodiment, fitting comprises using Metropolis-Hastings MCMC.

In an embodiment, fitting comprises using a non-Bayesian approach, e.g., a frequentist approach, e.g., using least squares fitting.

In an embodiment, g is determined by determining the fit of values for VAFI, p, C, and M to a model for somatic/germline status.

In an embodiment, the method comprises acquiring an indication of heterozygosity for said variant, e.g., mutation.

In an embodiment, sample purity (p) is global purity, e.g., is the same for all genomic segments.

In an embodiment, the value of g is acquired by:

$$AF = \frac{pM + g(1-p)}{pC + 2(1-p)},$$

where AF is allele frequency.

In an embodiment, a value of g that is close to 0, e.g., does not differ significantly from 0, indicates the variant is a somatic variant.

In an embodiment, a value of g that is 0, or close to 0, e.g., within a predetermined distance from 0, e.g., a value of g of less than 0.4, indicates the variant is a somatic variant.

In an embodiment, a value of g that is close to 1, e.g., does not differ significantly from 1, indicates the variant is a germline variant.

In an embodiment, a value of g that is 1, or close to 1, e.g., within a predetermined distance from 1, e.g., a value of g of more than 0.6, indicates the variant is a germline variant.

In an embodiment, a value of g is less than 1 but more than 0, e.g., if it is less than 1 by a predetermined amount and more than 0 by a predetermined amount, e.g., if g is between 0.4 and 0.6, it indicates an indistinguishable result.

In an embodiment, a value of g that is significantly less than 0, is indicative of a subclonal somatic variant.

In an embodiment, the value of g is acquired by:

$$AF = \frac{pM' + g(1-p)}{pC + 2(1-p)},$$

where AF is allele frequency, and M'=C−M (e.g., when M is a non-minor allele frequency), e.g., the variant is a germline polymorphism if g=1 and the variant is a somatic mutation if g=0.

In an embodiment, the somatic/germline status is determined, e.g., when the sample purity is below about 40%, e.g., between about 10% and 30%, e.g., between about 10% and 20%, or between about 20% and 30%.

In an embodiment, when:
a value of M equal to 0 not equal to C is indicative of absence of the variant, e.g., mutation, e.g., not existent in the tumor;
a non-zero value of M equal to C is indicative of homozygosity of the variant, e.g., mutation, e.g., with loss of heterozygosity (LOH);
a value of M equal to 0 equal to C indicates a homozygous deletion of the variant, e.g., mutation, e.g., not existent in the tumor; and
a non-zero value of M not equal to C is indicative of heterozygosity of the variant, e.g., mutation.

In an embodiment, the method comprises acquiring an indication of zygosity for said variant, e.g., mutation.

In an embodiment, the mutation status is determined as homozygous (e.g., LOH) if M=C≠0.

In an embodiment, the mutation status is determined as homozygous deletion if M=C=0.

In an embodiment, the mutation status is determined as heterozygous is 0<M<C.

In an embodiment, the mutation is absent from the tumor if M=0 and C≠0.

In an embodiment, the zygosity is determined, e.g., when the sample purity is greater than about 80%, e.g., between about 90% and 100%, e.g., between about 90% and 95%, or between about 95% and 100%.

In an embodiment, the control is a sample of euploid (e.g., diploid) tissue from a subject other than the subject from which the tumor sample is from, or a sample of mixed euploid (e.g., diploid) tissues from one or more (e.g., at least 2, 3, 4, or 5) subjects other than the subject from which the tumor sample is from.

In an embodiment, the method comprises sequencing each of the selected subgenomic intervals and each of the selected germline SNPs, e.g., by next generation sequencing (NGS).

In an embodiment, the sequence coverage prior to normalization is at least about 10×, 20×, 30×, 50×, 100×, 250×, 500×, 750×, or 1000× the depth of the sequencing.

In an embodiment, the subject has received an anti-cancer therapy.

In an embodiment the subject has received an anti-cancer therapy and is resistant to the therapy or exhibits disease progression.

In an embodiment the subject has received an anti-cancer therapy which is selected from: a therapeutic agent that has been approved by the FDA, EMEA, or other regulatory agency; or a therapeutic agent that has been not been approved by the FDA, EMEA, or other regulatory agency.

In an embodiment the subject has received an anti-cancer therapy in the course of a clinical trial, e.g., a Phase I, Phase II, or Phase III clinical trial (or in an ex-US equivalent of such a trial).

In an embodiment the variant is positively associated with the type of tumor present in the subject, e.g., with occurrence of, or resistance to treatment.

In an embodiment the variant is not positively associated with the type of tumor present in the subject.

In an embodiment the variant is positively associated with a tumor other than the type of tumor present in the subject.

In an embodiment the variant is a variant that is not positively associated with the type of tumor present in the subject.

In an embodiment, the method can memorialize, e.g., in a database, e.g., a machine readable database, provide a report containing, or transmit, a descriptor for one or more of: the presence, absence, or frequency, of other mutations in the tumor, e.g., other mutations associated with the tumor type in the sample, other mutations not associated with the tumor type in the sample, or other mutations associated with a tumor other than the tumor type in the sample; the characterization of the variant; the allele or gene; or the tumor type, e.g., the name of the type of tumor, whether the tumor is primary or secondary; a subject characteristic; or therapeutic alternatives, recommendations, or choices.

In an embodiment a descriptor relating to the characterization of the variant comprises a descriptor for zygosity or germline vs somatic status.

In an embodiment a descriptor relating to a subject characteristic comprises a descriptor for one or more of: the subject's identity; one or more of the subject's, age, gender, weight, or other similar characteristic, occupation; the subject's medical history, e.g., occurrence of the tumor or of other disorders; the subject's family medical history, e.g., relatives who share or do not share the variant; or the subject's prior treatment history, e.g., the treatment received, response to a previously administered anti-cancer therapy, e.g., disease resistance, responsiveness, or progression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE DRAWINGS

The drawings are first described.

FIG. 7 provides a Table of expected allele frequencies showing that the ability to distinguish somatic variants versus germline polymorphisms, and the ability to determine zygosity status are dependent upon sample purity.

FIG. 8 depicts a subset of the Table shown in FIG. 7 with the LOH status indicated.

DETAILED DESCRIPTION

Figure 1:
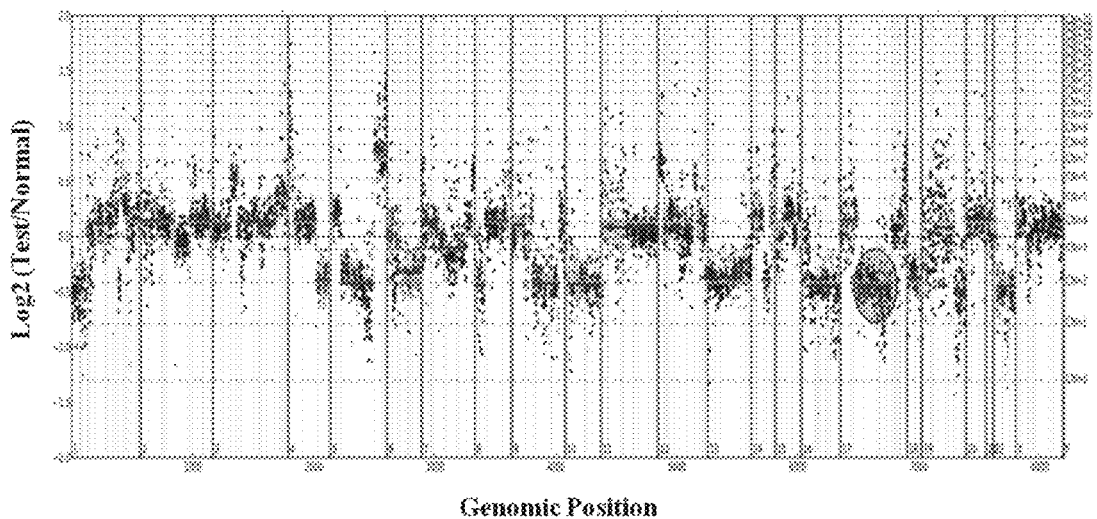
FIG. 1 depicts an exemplary CGH-like log-ratio profile of sample to acquire Input SCI. The region that encompasses BRCA1 gene is circled.

Certain terms are first defined. Additional terms are defined throughout the specification.

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by one or more or all of: "directly acquiring," "indirectly acquiring" the physical entity or value, or in the case of a value, "acquiring by calculation."

"Directly acquiring" means performing a process (e.g., performing a synthetic or analytical method) to obtain the physical entity or value. "Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

"Indirectly acquiring" refers to receiving the physical entity or value from another party or source (e.g., a third party laboratory that directly acquired the physical entity or value). E.g., a first party may acquire a value from a second party (indirectly acquiring) which said second party directly acquired or acquired by calculation.

"Acquiring by calculation" refers to acquiring a value by calculation or computation, e.g., as performed on a machine, e.g., a computer.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above. Methods described herein can include acquiring the tumor sample.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high throughput fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample. Method described herein can use NGS methods.

"Nucleotide value" as referred herein, represents the identity of the nucleotide(s) occupying or assigned to a preselected nucleotide position. Typical nucleotide values include: missing (e.g., deleted); additional (e.g., an insertion of one or more nucleotides, the identity of which may or may not be included); or present (occupied); A; T; C; or G. Other values can be, e.g., not Y, wherein Y is A, T, G, or C; A or X, wherein X is one or two of T, G, or C; T or X, wherein X is one or two of A, G, or C; G or X, wherein X is one or two of T, A, or C; C or X, wherein X is one or two of T, G, or A; a pyrimidine nucleotide; or a purine nucleotide. A nucleotide value can be a frequency for one or more, e.g., 2, 3, or 4, bases (or other value described herein, e.g., missing or additional) at a nucleotide position. E.g., a nucleotide value can comprise a frequency for A, and a frequency for G, at a nucleotide position.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Sample," "tumor sample," "cancer sample," "tissue sample," "patient sample," "patient cell or tissue sample" or "specimen" each refers to a collection of cells obtained from a subject or patient, e.g., from a tissue, or circulating cells, of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. Typically, the sample is a tumor sample, e.g., includes one or more premalignant or malignant cells. In certain, embodiments, the sample, e.g., the tumor sample, is acquired from a solid tumor, a soft tissue tumor or a metastatic lesion. In other embodiments, the sample, e.g., the tumor sample, includes tissue or cells from a surgical margin. In an embodiment, the sample, e.g., tumor sample, includes one or more circulating tumor cells (CTC) (e.g., a CTC acquired from a blood sample). In other embodiments, the sample is a tumor sample, e.g., includes one or more premalignant or malignant cells. In certain, embodiments, the sample, e.g., the tumor sample, is acquired from a solid tumor, a soft tissue tumor or a metastatic lesion. In other embodiments, the sample, e.g., the tumor sample, includes tissue or cells from a surgical margin. The sample can be histologically normal tissue. In another embodiment, the sample, e.g., tumor sample, includes one or more circulating tumor cells (CTC) (e.g., a CTC acquired from a blood sample). In one embodiment, the method further includes acquiring a sample, e.g., a tumor sample as described herein. The sample can be acquired directly or indirectly.

"Sequencing" a nucleic acid molecule requires determining the identity of at least one nucleotide in the molecule. In embodiments the identity of less than all of the nucleotides in a molecule are determined. In other embodiments, the identity of a majority or all of the nucleotides in the molecule is determined.

"Subgenomic interval" as referred to herein, refers to a portion of genomic sequence. In an embodiment a subgenomic interval can be a single nucleotide position, e.g., a nucleotide position variants of which are associated (positively or negatively) with a tumor phenotype. In an embodiment a subgenomic interval comprises more than one nucleotide position. Such embodiments include sequences of at least 2, 5, 10, 50, 100, 150, or 250 nucleotide positions in length. Subgenomic intervals can comprise an entire gene, or a preselected portion thereof, e.g., the coding region (or portions thereof), a preselected intron (or portion thereof) or exon (or portion thereof). Typically a subgenomic interval will include or be an exon. A subgenomic interval can comprise all or a part of a fragment of a naturally occurring, e.g., genomic, nucleic acid. E.g., a subgenomic interval can correspond to a fragment of genomic DNA which is subjected to a sequencing reaction. In embodiments a subgenomic interval is continuous sequence from a genomic source. In embodiments a subgenomic interval includes sequences that are not contiguous in the genome, e.g., it can include junctions formed found at exon-exon junctions in cDNA.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, e.g., a promoter, an enhancer, a 5' untranslated region (5' UTR), or a 3' untranslated region (3' UTR), or a fragment thereof; a cDNA or a fragment thereof; a polymorphism; an SNP; a somatic mutation, a germ line mutation or both; an alteration, e.g., a point or a single mutation; a deletion mutation (e.g., an in-frame deletion, an intragenic deletion, a full gene deletion); an insertion mutation (e.g., intragenic insertion); an inversion mutation (e.g., an intra-chromosomal inversion); a linking mutation; a linked insertion mutation; an inverted duplication mutation; a tandem duplication (e.g., an intrachromosomal tandem duplication); a translocation (e.g., a chromosomal translocation, a non-reciprocal translocation); a rearrangement (e.g., a genomic rearrangement (e.g., a rearrangement of one or more introns, or a fragment thereof; a rearranged intron can include a 5'- and/or 3'-UTR); a change in gene copy number; a change in gene expression; a change in RNA levels, or a combination thereof. The "copy number of a gene" refers to the number of DNA sequences in a cell encoding a particular gene product. Generally, for a given gene, a mammal has two copies of each gene. The copy number can be increased, e.g., by gene amplification or duplication, or reduced by deletion.

"Variant," as used herein, refers to a structure that can be present at a subgenomic interval that can have more than one structure, e.g., an allele at a polymorphic locus.

Headings, e.g., (a), (b), (i) etc, are presented merely for ease of reading the specification and claims. The use of headings in the specification or claims does not require the steps or elements be performed in alphabetical or numerical order or the order in which they are presented.

Sequence Coverage Input (SCI)

Input SCI is a measure of normalized sequence coverage at each of a plurality of selected subgenomic intervals, e.g., exons. SCI can comprise a series of values for a plurality of selected subgenomic intervals. A useful formulation of SCI is a function, e.g., the log, of a value related to the number of sequencing reads for a subgenomic interval, e.g., an exon, in the tumor sample/a value related to the number of sequencing reads for that subgenomic interval in the control. This is sometimes referred to herein as log r. A useful form for SCI is:

$\log_2$ (the # of sequencing reads for a subgenomic interval, e.g., an exon, in the tumor sample/the # of sequencing reads for that subgenomic interval in the control).

E.g., for a particular subgenomic interval, e.g., an exon, reads are acquired. Reads for that subgenomic interval from a control diploid cell are acquired. The log of the ratio of the former to the later is acquired. This is repeated for each of a plurality of subgenomic intervals. The resulting series of log r values can be used as SCI.

The measure of normalized sequence coverage can also comprise adjustment for other parameters that might distort the analysis. E.g., if it were found that values for measure of normalized sequence coverage correlated with another factor, e.g., GC content, the method can include the use of an SCI that is corrected for this. In an embodiment the GC content for a plurality of the subgenomic intervals is acquired. The GC content and log r can be compared to determine if they are correlated. This can be undesirable as variations in log r should generally be independent of GC content. Then if there is a correlation, the values for log r can be adjusted, e.g., by regression analysis.

SNP Allele Frequency Input (SAFI)

Input SCI comprises a measure of the allele frequency for each of a plurality of selected germline SNPs in the tumor sample. An allele frequency at a selected SNP can be acquired from reads from the sample which cover a selected SNP. In embodiment the allele frequency is the frequency of the minor allele as portrayed in the reads. In other embodiments the allele frequency is the frequency, as portrayed in the reads, of an alternative allele. The identity of an alternative allele can be acquired from a reference database, e.g., UCSC Human Genome Browser (Meyer L. R., et al., The UCSC Genome Browser database: extensions and updates 2013. *Nucleic Acids Res.* 2013; 41(Database issue): D64-69), and dbSNP (Sherry S. T., et al., dbSNP: the NCBI database of genetic variation. *Nucleic Acids Res.* 2001; 29(1): 308-311).

Variant Allele Frequency Input (VAFI)

Input VAFI comprises the allele frequency for said variant, e.g., mutation, in the tissue or sample, e.g., tumor sample.

Control

Typically, the number of reads for each of a plurality of subgenomic intervals is normalized, e.g., to the number of reads from a control. The control need not be, and typically is not, from the subject that supplies the tumor sample. The control sample can be from an individual that does not have a tumor, or does not have a tumor of the type in the subject sample. Typically the sample is from normal, non-disease state tissue. A control is "process-matched" with the tumor sample if they are sequenced under similar conditions. E.g., a process matched control can be one in which one or more or all of the following conditions for the treatment of the tumor sample and the control are met: they prepared in the same way; nucleic acid for sequencing is obtained from them in the same way; they are sequenced with the same sequencing method; or they are sequenced in the same run.

Genomic Segments

A genomic segment comprises a subgenomic interval, e.g., an exon, and other genomic sequence, e.g., one or a plurality of other subgenomic intervals. Typically, a genomic interval will include a plurality of subgenomic intervals, e.g., exons, which are characterized by having one or both of:

a measure of normalized sequence coverage, e.g., log r, that differ by no more than a preselected amount, e.g., the values for $\log_2$ r for subgenomic intervals, e.g., exons, within the boundaries of the genomic segment differ by no more than a reference value, or are substantially constant; and SNP allele frequencies for germline SNPs that differ by no more than a preselected amount, e.g., the values for germline SNP allele frequencies for subgenomic intervals, e.g., exons, within the boundaries of the genomic segment differ by no more than a reference value, or are substantially constant.

Assembly of genomic sequences into genomic segments can in cases be viewed as a data reduction step. E.g., several thousand exons may amount to many fewer, e.g., a hundred or fewer, genomic segments. The number of subgenomic intervals, e.g., exons, that are contained in, or are combined to form, the genomic segments can at least 2, 5, 10, 15, 20, 50 or 100 times the number of genomic segments. In embodiments the number of subgenomic intervals, e.g., exons, is at least 3, 4, 5, 6, 7, 8, 9, 10, 11, 12, 13, 14, or 15 times the number of genomic segments.

Genomic sequences, e.g., subgenomic intervals, e.g., exons, can be assembled into subgenomic intervals, with a method described herein, e.g., a method comprising a circular binary segmentation (CBS) (Olshen et al. Biostatistics. 2004; 5(4): 557-572). Other methods that can be used include, but not limited to, HMM based methods (Fridlyand et al. *Journal of Multivariate Analysis* 90 (2004): 132-153), Wavelet based methods (Hsu et al. *Biostatistics.* 2005; 6(2): 211-226), and Cluster along Chromosomes method (Wang et al. *Biostatistics.* 2005; 6(1): 45-58).

Statistical Model

Genome-wide copy number, as well as copy number and LOH estimates for each chromosomal segment, can be determined by fitting a statistical model, e.g., a statistical model described herein.

For example, the following steps can be performed:

Let:

$S_i$ be a genomic segment $l_i$ be the length of $S_i$ $r_{ij}$ be the log ratio (LR) of exon j within $S_i$ $f_{ik}$ be the minor allele frequency of SNP $\underline{k}$ within $S_i$ Seek to estimate p—tumor purity, and $C_i$—the copy numbers of $S_i$ Jointly model $r_{ij}$ and $f_{ik}$, given p and $C_i$;

$$r_{ij} \sim N\left(\log_2 \frac{p*C_i + (1-p)*2}{p*\left(\sum_i l_i C_i\right)/\sum_i l_i + (1-p)*2}, \sigma_{ri}\right)$$

$$f_{ik} \sim N\left(\frac{p*Mi + (1-p)*1}{p*Ci + (1-p)*2}, \sigma fi\right)$$

$M_i \leq C_i$ is number of altered alleles at $S_i$ $\sigma_{ri}$ and $\sigma_{fi}$ are noise parameters Fit model using standards methods, e.g., Markov chain Monte Carlo (MCMC), assignming copy numbers to all segments.

For each genomic segment i:

If $C_i = M_i = 0$, the segment has homozygous deletion in tumor;

If $C_i = M_i \neq 0$, the segment has LOH in tumor;

If $C_i \neq M_i \neq 0$, the segment is heterozygous in tumor.

For each mutation identified, use model fit to assess differences in expected allele frequencies (AF) between germline, somatic, and subclonal somatic mutations. Statistical confidence assessed based on read depth and local variability in allele frequency estimates.

For example, a gemline variant at segment i can have expected AF:

$$AFgermline = \frac{pMi + (1-p)}{pCi + 2(1-p)},$$

a somatic mutation at segment i can have expected AF:

$$AFsomatic = \frac{pMi}{pCi + 2(1-p)},$$

and a subclonal somatic mutation at segment i can have expected AF:

$$AF_{somatic} \ll \frac{pM_i}{pC_i + 2(1-p)}.$$

Figure 7:
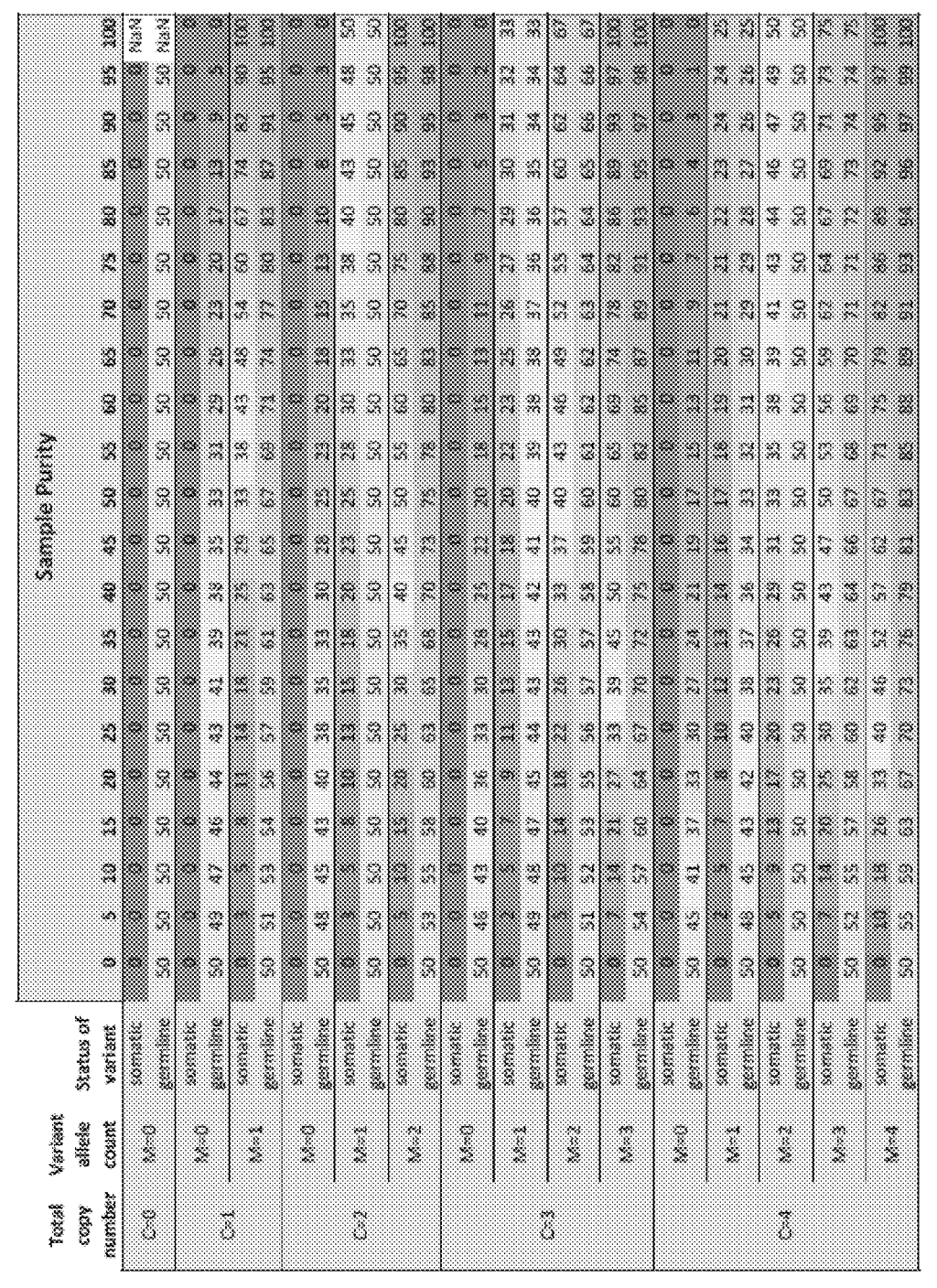

FIG. 8 is an exemplary expected allele frequency table for copy numbers, given purity (p), copy number (C), and alternative allele count (M). For example, low purity (e.g., <20%) samples are relatively be easier for assessing somatic status, but more difficult in assessing tumor LOH. As another example, high purity (e.g., >90%) samples are easier for assessing tumor LOH, but more difficult in assessing somatic status. Tumor samples that are well-admixed with surrounding normal tissue (e.g., many clinical cancer specimens) can be optimal. A more comprehensive table for expected allele frequencies is depicted in FIG. 7.

Variants and SNPs

The methods described herein can be used to characterize variants found anywhere in the genome including in exons, introns, 5'-UTRs, and inter-gene regions.

In an embodiment, the method comprises characterizing a variant, e.g., a mutation, in a tumor suppressor gene. In another embodiment, the method comprises characterizing a variant, e.g., a mutation, in an oncogene.

In an embodiment, the method comprises characterizing a variant, e.g., a mutation, in a gene selected from: Table 1, Table 2, or Table 3.

In an embodiment, the method comprises acquiring an SCI for subgenomic intervals from at least five, six, seven, eight, nine, ten, fifteen, twenty, twenty-five, thirty or more genes from the sample, wherein the genes are chosen from: Table 1, Table 2, or Table 3.

In an embodiment, the method comprises acquiring an SCI for a plurality, e.g., at least 2, 3, 4, 5, 6, 7, 8, 9, 10, 15, 20, of subgenomic intervals, e.g., exons, a gene chosen from: Table 1, Table 2, or Table 3.

In an embodiment, the method comprises acquiring an SAFI for a SNP from at least five, six, seven, eight, nine, ten, fifteen, twenty, twenty-five, thirty or more genes from the sample, wherein the genes or gene products are chosen from: Table 1, Table 2, or Table 3.

TABLE 1

Exemplary Genes for Analysis

ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, and TP53.

TABLE 2

Exemplary Genes for Analysis

ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124,

TABLE 2-continued

Exemplary Genes for Analysis

GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, and WT1.

TABLE 3

Exemplary Genes for Analysis

ABCB1, ABCC2, ABCC4, ABCG2, ABL1, ABL2, AKT1, AKT2, AKT3, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1, SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TOP1, TP53, TPMT, TSC1, TSC2, TYMS, UGT1A1, UMPS, USP9X, VHL, and WT1.

In one embodiment, one or more of the genomic segments (e.g., SNPs) are relevant to pharmacogenetics and pharmacogenomics (PGx), e.g., drug metabolism and toxicity.

Cancers

The method can be used to analyze variants in subjects having cancer.

Cancers include, but are not limited to, B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In some embodiments, the cancer is a primary cancer, e.g., a cancer is named after the part of the body where it first started to grow. In some embodiments, the cancer is a secondary cancer (or a metastasis), e.g., when cancer cells spread from the primary cancer to another part of the body (e.g., lymph nodes, lungs, liver, brain, and bones). For example, a secondary cancer can contain cancer cells originated from the primary cancer site.

Sample Processing, Analysis, Interpretation and Reporting

The specimens can be processed and analyzed using NGS-based cancer assay, e.g., as described in Frampton et al. *Nat Biotechnol*. 31(11):1023-1031 (2013). Typically, the method includes, e.g., DNA extraction, sequencing, analysis and interpretation.

DNA can be extracted from FFPE tumor samples. Typical sample requirements include, e.g., surface area ≥25 mm$^2$, sample volume ≥1 mm$^3$, nucleated cellularity ≥80% or 30,000 cells, tumor content ≥20%.

Sequencing library can be prepared using "with-bead" library construction. DNA can be fragmented by sonication and ≥50 ng of dsRNA (e.g., quantified by PicoGreen) may be required for library preparation. DNA fragments can be captured by biotinylated DNA oligonucleotides during hybridization. Sequencing can be performed, e.g., to >500× average unique coverage (e.g., with >100× at >99% exons), e.g., on a HiSeq platform (Illumina) using 49×49 paired-end sequencing.

Various types of analysis can be performed. For example, base substitutions and short insertions/deletions can be analyzed by Bayesian algorithm and local assembly, respectively. As another example, copy number alterations (CNAs) can be assessed by comparison with process-matched normal control and gene fusions can be identified by analysis of chimeric read pairs. The methods described herein can be sensitive, e.g., to variants present at any mutant allele frequency. Detection of long (e.g., 1-40 bp) indel variants can be achieved using Bruijin graph-based local assembly. CGH-like analysis of read-depth can be used for assessment of CNAs.

The methods described herein allow for clinical interpretation without a matched normal. The reporting approach can include, e.g., removal of germline variants (e.g., from 1000 Genome Project (dbSNP135)) and highlighting known driver alterations (e.g., COSMIC v62) as biologically significant. A concise summary of the biomedical literature and current clinical trials can be provided for each highlighted alteration.

Example System Environment

According to some embodiments, specially configured computer systems can be configured to perform the analysis discussed herein, e.g., to generate characterization models of genetic variants appearing in tumor samples. The characterization models can specify, for example, a tumor type (e.g., somatic, germline, subclonal somatic, and not-distinguishable) and/or a tumor zygosity (e.g., homozygous, heterozygous, and absent) for a genetic variant based on sequencing information obtained on the sample. Various embodiments of characterization systems can be configured to operate on testing data (e.g., genetic sequencing information) provided from genetic screening systems and/or methods. In some embodiments, the characterization systems can also be configured to perform genetic testing on tumor samples directly to generate, for example, genetic sequencing information. In further embodiments, characterization models can be generated by system components that interact with system components for sequencing and/or testing tumor samples. The results generated by sequencing components can be accessed by characterization system components to generate characterization models of genetic variants.

According to some embodiments, characterization systems can provide user or collaborator (e.g., physicians, researches, clinicians, and other medical personnel) access to genomic sequencing data or information on variants through user interfaces. Responsive to selection in the user interface, the system can accept definition of subgenomic intervals and/or germline single nucleotide polymorphisms (SNPs) within a tumor sample on which to provide a characterization model. In other embodiments, the characterization system can automatically define the subgenomic intervals and/or germline SNPs on which to develop classification analysis.

According to one embodiment, a characterization system is configured to capture data on a genomic sequence coverage for specified subgenomic intervals. The system can define a variable for a sequence coverage input ("SCI" discussed herein) based on the values for sequence coverage at the specified subgenomic intervals. In one example, the system includes a user interface display configured to accept user input to define the specified subgenomic intervals. In other embodiments, the subgenomic intervals can be pre-defined as part of genetic testing and/or analysis. Further, the system can also be configured to identify the subgenomic intervals to analyze automatically (e.g., based on segmentation analysis, etc). Once the subgenomic intervals are specified, the system captures a value for sequence coverage for each of a plurality of specified subgenomic intervals. The captured values can be normalized, averaged, or weighted to prevent outlier values from skewing subsequent calculations. In one example, a normalized value for sequence coverage is used in generating a characterization model for a tumor sample.

The characterization system can also be configured to derive an allele frequency value according to specification of germline SNPs in the tumor sample. The system can define a variable for an SNP allele frequency input ("SAFI" as discussed herein) based on the values for allele frequency for the selected germline SNPs. In some embodiments, the system specifies the germline SNPs on which to capture values for allele frequency (e.g., based on pre-specified selection, automatically based on analysis of the tumor sample, etc.). In other embodiments, the user interface can also be configured to accept selection of germline SNPs within genetic sequencing information obtained on, for example, a tumor sample.

In some embodiments, the system can be configured to capture and/or calculate additional values from genetic sequence information (including, e.g., captured from testing systems and/or components or generated by the characterization system directly). In one example, the system can capture allele frequency in a tumor sample ("VAFI"—variant allele frequency as discussed herein) for a given variant (e.g., a mutation) from testing data. In another example, the system can generate the data for capturing the allele frequency responsive to genetic sequence testing performed on the sample. The additional values which can be captured and/or acquired can also include any one or more of genomic segment total copy number ("C"—discussed herein) for a plurality of genomic segments; a genomic segment minor allele copy number ("M"—discussed herein) for a plurality of genomic segments; and a sample purity value ("p"—discussed herein).

According to one embodiment, the characterization system can determine a tumor type (e.g., somatic, germline, subclonal somatic, and not-distinguishable), a tumor zygosity (e.g., homozygous, heterozygous, and absent) responsive to the genetic sequencing data. In embodiments this is achieved without resort to physical analysis of a control sample to determine for example purity.

For example, the system can calculate a value for a variant type, e.g., mutation type ("g"—e.g., a value that is indicative of a variant being somatic, germline, subclonal somatic, or not-distinguishable) by executing a function on the acquired and/or calculated values for VAFI, p, C, and M. Based on the output value of g, the system can classify the variant type, e.g., mutation type. In one example, a g value equal or approximately equal to 0 is classified by the system as somatic variant. In another example, a g value equal or approximately equal to 1 is classified by the system as a germline variant. Values of g between 0 and 1 (e.g., 0.4-0.6) are classified by the system as not-determinable.

In further examples, the system can calculate a value indicative of the zygosity of the variant in the sample as a function of the acquired and/or calculated values for C and M. For example, a value of M equal to 0 not equal to C is indicative of absence of the variant, a non-zero value of M equal to C is indicative of homozygosity of the variant (e.g., LOH), a value of M equal to 0 equal to C is indicative of homozygous deletion of the variant, and a non-zero value of M not equal to C is indicative of heterozygosity of the variant.

In some implementations, the system can also be configured to determine a confidence level associated with any calculation and/or calculated value (e.g., based on statistical analysis of the input(s) and computational values used to derive an output). The system can use determinations on the confidence of calculations and/or calculated values in interpreting classification outputs. In one example, the not-determinable range of values can be increased where the degree of confidence associated with the calculation of g is low. In another example, the not-determinable range of values can be decreased where the degree of confidence associated with the calculation of g is high.

Example Calculations

Various embodiments of the system for generating characterization models can perform any one or more of the functions and/or computations discussed herein. In some embodiments, the system includes system components specially configured calculate C, M, and/or p responsive to fitting a genome-wide copy number model to one or both of the SCI and the SAFI. In one example, the system and/or system components are configured to fit the genome-wide copy number model to the SCI using the equation of:

$$\log Ratio_i = \log_2 \frac{pC_i + 2(1-p)}{p\psi + 2(1-p)},$$

where $\psi$ is tumor ploidy. The system and/or system components can calculate $\psi$ as $=(\Sigma l_i C_i)/\Sigma l_i$, where $l_i$ is the length of a genomic segment. The system can also be configured to fit the genome-wide copy number model to the SAFI using the equation of:

$$AF = \frac{pM + 1(1-p)}{pC + 2(1-p)},$$

where AF is allele frequency. In one example, the system calculates g based on the fit of values for VAFI, p, C, and M to models of somatic/germline status. Various fitting methodologies can be executed by the system to determine g values (e.g., Markov chain Monte Carlo (MCMC) algorithm, e.g., ASCAT (Allele-Specific Copy Number Analysis of Tumors), OncoSNP, or PICNIC (Predicting Integral Copy Numbers In Cancer).

Figure 3:
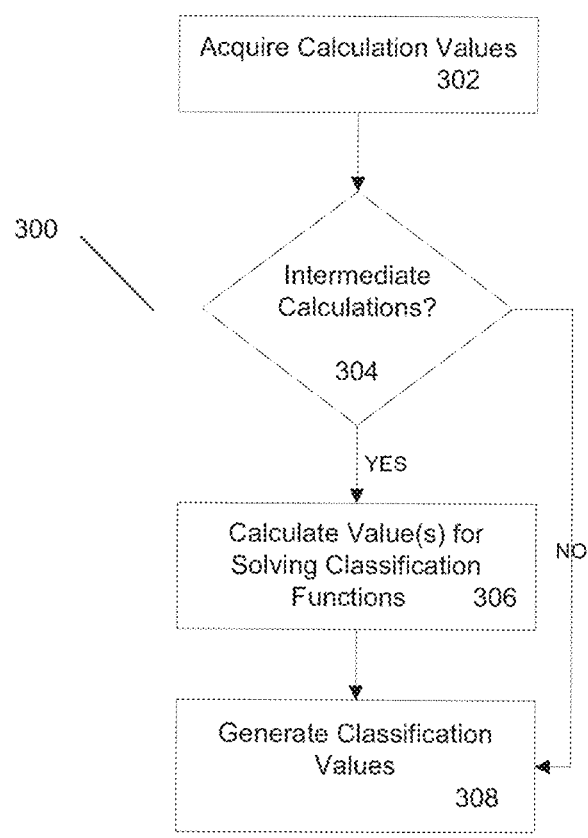
FIG. 3 is a process flow chart for determining a characterization model for a tumor sample according to one embodiment.

According to one embodiment, a system for determining a characterization model for a tumor sample can execute a variety of functions and/or processes. Shown in FIG. 3 is an example process 300 for generating a characterization model for a tumor sample according to one embodiment. Process 300 begins at 302 by acquisition of calculation values. The acquisition of the calculation values at 302 can include accessing any one or more of the values used to calculate g and/or determine zygosity (e.g., from evaluation of M against C). For example, the calculation values accessed at 302 can include any one or more of: SCI, SAFI, VAFI, C, M, p. In some implementations, acquisition at 302 can also include calculation and/or direct determination of SCI, SAFI, and VAFI from sequencing on a tumor sample. Additionally, acquisition at 302 can also include calculation and/or direct determination of C, M, and/or p.

Process 300 continues at 304, where values necessary for determining the characterization model that are missing (304YES) are calculated from the acquired values of 302. For example, C, M, and/or p can be calculated at 306 if any of the values are not acquired, and intermediate calculations are necessary 304YES. If the values necessary for classification are acquired at 302, then intermediate calculations are not needed 304NO. Once the values necessary are defined, classification values can be determined at 308. In one example, a value indicative of variant type is determined at 308. The variant type can include somatic, germline, subclonal somatic, and/or not-distinguishable based on the value determined at 308. In one example, a value for g is determined at 308, and the variant type is classified based on the value of g (e.g., equal or approximately equal to 0: somatic; equal or approximately equal to 1: germline; less than 0; subclonal somatic; and in a range between 0 and 1 (e.g., 0.4 to 0.6) not-distinguishable).

In another example, a value indicative of zygosity as a function of C and M is determined at 308 (e.g., a value of M equal to 0 not equal to C is indicative of absence of the variant, a non-zero value of M equal to C is indicative of homozygosity of the variant (e.g., LOH), a value of M equal to 0 equal to C is indicative of a homozygous deletion of the variant, and a non-zero value of M not equal to C is indicative of heterozygosity of the variant). Based on the classification value(s) determined at 308 a characterization model can be generated for a variant specifying type and/or zygosity.

Various embodiments according to the disclosure may be implemented on one or more specially programmed computer systems. These computer systems may be, for example, general-purpose computers such as those based on Intel PENTIUM-type processor, Motorola PowerPC, AMD Athlon or Turion, Sun UltraSPARC, Hewlett-Packard PA-RISC processors, or any other type of processor, including multi-core processors. It should be appreciated that one or more of any type computer system may be used to perform a process or processes for generating a characterization model for a variant in a tumor sample. Further, the system may be located on a single computer or may be distributed among a plurality of computers attached by a communications network.

A general-purpose computer system according to one embodiment is specially configured to perform any of the described functions, including but not limited to, acquiring calculation values (e.g., SCI, SAFI, VAFI, M, C, p), normalizing calculation values against a control, calculating intermediate values, calculating classification value(s) (e.g., g and/or zygosity value(s)), etc. Additional functions include, for example, fitting genomic wide models to determine classification values, determining log r values, determining correlation of GC content, specifying genomic intervals, specifying germline SNPs, determining calculation values (e.g., SCI, SAFI, VAFI, M, C, p), defining genomic segments, segmenting genomic sequence information, determining sequence coverage, determining SNP allele frequencies, determining genomic segment boundaries, etc.

It should be appreciated that the system may perform other functions, including assembling sequences for subgenomic intervals, generating genome-wide copy number model(s), fitting genome-wide copy number model(s), displaying genomic sequence information for selection, determining sample purity, calculating confidence values, and enforcing thresholds on calculations (e.g., purity >80%).

The functions, operations, and/or algorithms described herein can also be encoded as software executing on hardware that together define a processing component, that can further define one or more portions of a specially configured general purpose computer, that reside on an individual specially configured general purpose computer, and/or reside on multiple specially configured general purpose computers.

Figure 4:
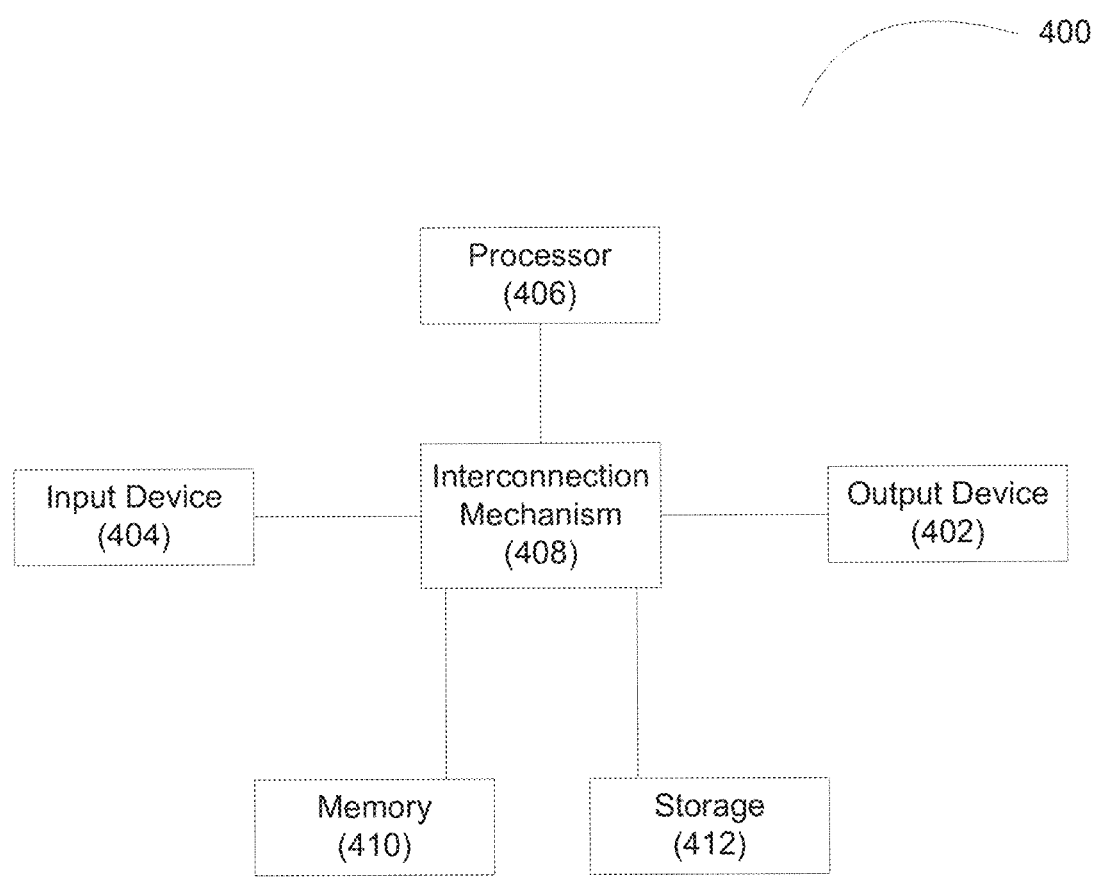
FIG. 4 shows an exemplary block diagram of a general-purpose computer system 400 which can be specially configured to practice various aspects of the present disclosure discussed herein.

FIG. 4 shows an example block diagram of a general-purpose computer system 400 which can be specially configured to practice various aspects of the present disclosure discussed herein. For example, various aspects of the disclosure can be implemented as specialized software executing in one or more computer systems including general-purpose computer systems 604, 606, and 608 communicating over network 602 shown in FIG. 6. Computer system 400 may include a processor 406 connected to one or more memory devices 410, such as a disk drive, memory, or other device for storing data. Memory 410 is typically used for storing programs and data during operation of the computer system 400. Components of computer system 400 can be coupled by an interconnection mechanism 408, which may include one or more busses (e.g., between components that are integrated within a same machine) and/or a network (e.g., between components that reside on separate discrete machines). The interconnection mechanism 408 enables communications (e.g., data, instructions) to be exchanged between system components of system 400.

Computer system 400 may also include one or more input/output (I/O) devices 402-204, for example, a keyboard, mouse, trackball, microphone, touch screen, a printing device, display screen, speaker, etc. Storage 412, typically includes a computer readable and writeable nonvolatile recording medium in which instructions are stored that define a program to be executed by the processor or information stored on or in the medium to be processed by the program.

Figure 5:
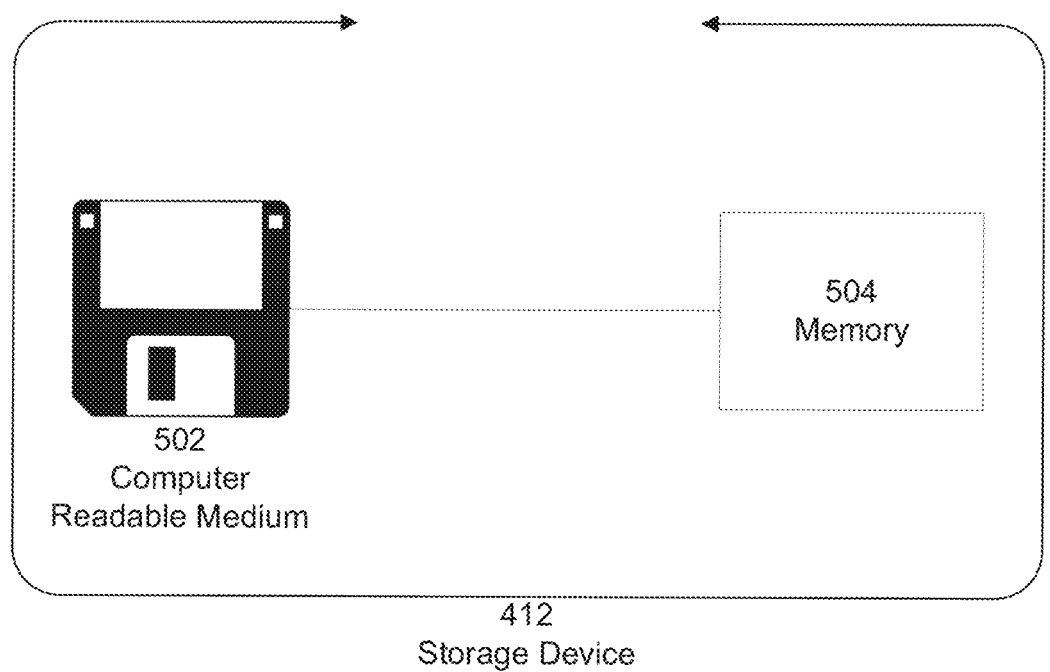
FIG. 5 depicts a storage device.

The medium may, for example, be a disk 502 or flash memory as shown in FIG. 5. Typically, in operation, the processor causes data to be read from the nonvolatile recording medium into another memory 504 that allows for faster access to the information by the processor than does the medium. This memory is typically a volatile, random access memory such as a dynamic random access memory (DRAM) or static memory (SRAM). In one example, the computer-readable medium is a non-transient storage medium.

Referring again to FIG. 4, the memory can be located in storage 412 as shown, or in memory system 410. The processor 406 generally manipulates the data within the memory 410, and then copies the data to the medium associated with storage 412 after processing is completed. A variety of mechanisms are known for managing data movement between the medium and integrated circuit memory element and the disclosure is not limited thereto. The disclosure is not limited to a particular memory system or storage system.

The computer system may include specially-programmed, special-purpose hardware, for example, an application-specific integrated circuit (ASIC). Aspects of the disclosure can be implemented in software executed on hardware, hardware or firmware, or any combination thereof. Although computer system 400 is shown by way of example as one type of computer system upon which various aspects of the disclosure can be practiced, it should be appreciated that aspects of the disclosure are not limited to being implemented on the computer system as shown in FIG. 4. Various aspects of the disclosure can be practiced on one or more computers having a different architectures or components than that shown in FIG. 4.

It should also be appreciated that the disclosure is not limited to executing on any particular system or group of systems. Also, it should be appreciated that the disclosure is not limited to any particular distributed architecture, network, or communication protocol.

Various embodiments of the disclosure can be programmed using an object-oriented programming language, such as Java, C++, Ada, or C# (C-Sharp). Other object-oriented programming languages may also be used. Alternatively, functional, scripting, and/or logical programming languages can be used. Various aspects of the disclosure can be implemented in a non-programmed environment (e.g., documents created in HTML, XML or other format that, when viewed in a window of a browser program, render aspects of a graphical-user interface (GUI) or perform other functions). The system libraries of the programming languages are incorporated herein by reference. Various aspects of the disclosure can be implemented as programmed or non-programmed elements, or any combination thereof.

Various aspects of the disclosure can be implemented by one or more systems similar to system 400. For instance, the system can be a distributed system (e.g., client server, multi-tier system) comprising multiple general-purpose computer systems. In one example, the system includes software processes executing on a system for generating a characterization model. Various system embodiments can execute operations such as accepting a tumor sample, executing genomic sequencing, generating and displaying classification/characterization information on the sample, generating user interfaces for displaying classification information, accepting user input regarding genomic segments and/or boundary definition, among other options. The system embodiments may operate as "black box" systems where an input sample is classified without further interaction, and other system embodiments may permit user interaction to specify genomic segments, genomic intervals, etc., on which analysis is performed.

There can be other computer systems that perform functions such as fitting genomic data to genome-wide copy number models, generating characterization models, storing characterization models, etc. These systems can also be configured to manage administration of testing of samples, accept samples as inputs, sequence samples, provide sequencing data to classification components, among other options. These systems and/or system components can be distributed over a communication system such as the Internet. One such distributed network, as discussed below with respect to FIG. 6, can be used to implement various aspects of the disclosure.

Figure 6:
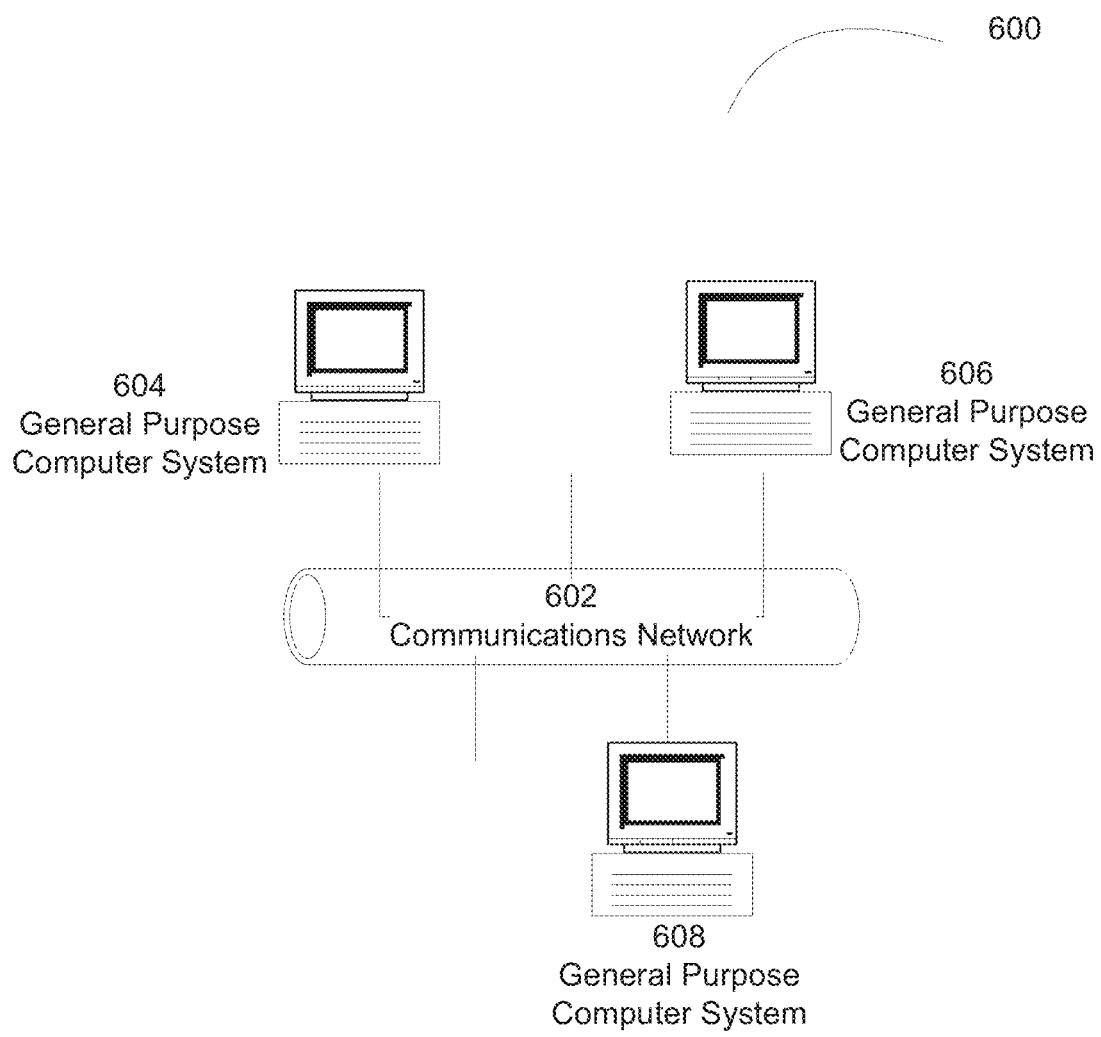
FIG. 6 depicts a networked computer system.

FIG. 6 shows an architecture diagram of an example distributed system 600 suitable for implementing various aspects of the disclosure. It should be appreciated that FIG. 6 is used for illustration purposes only, and that other architectures can be used to facilitate one or more aspects of the disclosure. System 600 may include one or more general-purpose computer systems distributed among a network 602 such as, for example, the Internet. Such systems may cooperate to perform any of the functions and/or processes discussed above.

In an example of one such system, one or more of systems 604, 606, and 608 may accept tumor samples, conduct genomic sequencing, and pass the resulting data to one or more of the remaining system 604, 606, and 608. It should be understood that the one or more client computer systems 604, 606, and 608 can also be used to access and/or update calculations for values to solve classification functions, and/or determine classification values, execute fitting algorithms, execute regression analysis, determine confidence values, etc.

In another example, a system 604 includes a browser program such as the Microsoft Internet Explorer application program, Mozilla's FireFox, or Google's Chrome browser through which one or more websites can be accessed. Further, there can be one or more application programs that are executed on system 604 that perform functions associated with evaluating a tumor sample, submitting a tumor sample, obtaining genomic sequencing data, and/or communicating genomic sequencing data. For example, system 604 may include one or more local databases for storing, caching and/or retrieving sequencing information associated with testing, sequencing, etc.

Network 602 may also include, one or more server systems, which can be implemented on general-purpose computers that cooperate to perform various functions discussed herein. System 600 may execute any number of software programs or processes and the disclosure is not limited to any particular type or number of processes. Such processes can be executed by system embodiments and/or system components to perform the various workflows and operations discussed.

Effect of Sample Purity on Analysis

The ability to distinguish somatic versus germline, and the ability to determine zygosity status are dependent upon sample purity. See FIG. 7 which provides a table of expected frequencies. The table enumerates values for the formula:

$$AF = \frac{pM + g(1-p)}{pC + 2(1-p)}$$

where p is "sample purity" (0%, 5%, 10%, 15%, 20% . . . ),
g is "status of variant", as described herein, e.g., g=0 being somatic, and g=1 being germline,
M is "variant allele count",
C is "total copy number",
AF are all the expected allele frequencies on the grid, and
NaN is "not a number", which occurs when the denominator pC+2(1−p) is precisely 0.

The limitations, based on sample purity, are as follows:
Low purity (p<20%) samples: Tumor zygosity assessment is difficult due to lack to tumor content. As an extreme example, if p=0%, there is no tumor specimen whatsoever, and one cannot assign a zygosity status at all. However, it's easy to distinguish somatic versus germline status here, because germline variants are expected have an allele frequency close to 50%, whereas somatic variants are expected to drastically differ from an allele frequency of 50%.

High purity (p>90%) samples: Somatic versus germline assessment is difficult due to lack of normal-cell content. As an extreme example, if p=100%, there is no normal cell whatsoever, and therefore we have zero germline information. However, it's easy to distinguish tumor zygosity, because we have an abundance of tumor information.

Other Embodiments

In other embodiments, the method, or the assay, further includes acquiring the sequence of a subgenomic interval that is present in a gene or gene product associated with one or more of drug metabolism, drug responsiveness, or toxicity (also referred to therein as "PGx" genes).

Methods described herein can comprise providing a report, e.g., in electronic, web-based, or paper form, to the patient or to another person or entity, e.g., a caregiver, e.g., a physician, e.g., an oncologist, a hospital, clinic, third-party payor, insurance company or government office, a research collaborator, or, generally, a party which is interested in the characterization of a variant.

EXAMPLES

Example 1: A Statistical Model for Detecting Gene Amplification and Homozygous Deletion from Targeted Next-Generation Sequencing of Clinical Cancer Specimens with Significant Stromal Admixture Molecular diagnostics are increasingly important to clinical oncology, as the number of therapies targeting specific genomic alterations grows. This trend has led to a proliferation of single biomarker assays or hotspot panels, restricted in the breadth of genes and classes of genomic alterations assessed. Limitations of these approached have been overcome in a CLIA certified, pan solid tumor, next-generation sequencing (NGS)-based test that interrogates the entire coding sequence of 182 selected cancer genes from minimal (≥50 ng) DNA from FFPE tissue. High coverage (>500×) and customized algorithms permit clinical-grade identification of all classes of genomic alterations. An approach to copy number assessment, which addresses the high stromal contamination in routine patient specimens and enables sensitive detection of focal gene amplifications and homozygous deletions, is discussed.

A CGH-like log-ratio profile of the sample is obtained by normalizing the sequence coverage obtained at all exons and >1,700 genome-wide SNPs against a process-matched normal control. This profile is segmented and interpreted using allele frequencies of sequenced SNPs to estimate tumor purity and copy number at each segment. Briefly, if $S_i$ is a genomic segment at constant copy number in the tumor, let $l_i$ be the length of $S_i$, $r_{ij}$ be the coverage measurement of exon j within $S_i$, and $f_{ik}$ be the minor allele frequency of SNP k within $S_i$. We seek to estimate p—tumor purity, and $C_i$—the copy numbers of $S_i$. We jointly model $r_{ij}$ and $f_{ik}$, given p and $C_i$:

$$r_{ij} \sim N\left(\log_2 \frac{p*C_i + (1-p)*2}{p*(\Sigma_i l_i C_i)/\Sigma_i l_i + (1-p)*2}, \sigma_{ri}\right)$$

and $$f_{ik} \sim N\left(\frac{p*M_i + (1-p)}{p*C_i + (1-p)*2}, \sigma_{fi}\right),$$

where $M_i$ is the copy number of minor alleles at $S_i$, distributed as integer $0 \leq M_i \leq C_i$, $\sigma_{ri}$ and $\sigma_{fi}$ reflect noise observed in the CGH and SNP data, respectively. Fitting is performed using Gibbs sampling, assigning absolute copy number to all segments. Focal amplifications are called at segments with ≥6 copies and homozygous deletions at 0 copies, in samples with purity >20%.

The method was validated against current clinical standards for copy number assessment: fluorescence in-situ hybridization (FISH) and immunohistochemistry (IHC). 42 Breast cancer specimens were analyzed with NGS-based and FISH/IHC calls for HER2 amplification and 22 Prostate cancer samples with calls for PTEN homozygous loss. Average sequence coverage in the dataset exceeded 1000×. Of the 6 HER2 amplified/36 normal and 6 PTEN deleted/16 normal cases by FISH/IHC, all but one were classified identically by NGS. Review of NGS data for the discordant NGS deleted/FISH normal PTEN call supported homozygous loss. Overall, relative to FISH/IHC, model accuracy for detecting focal gene amplification and homozygous deletion was thus 98% (63/64 calls). Importantly, nearly 40% (24/64) of cases had tumor purity ≤50%, including 4/13 (30%) of cases with a HER2 or PTEN alteration, highlighting the importance of addressing stromal contamination in clinical cancer specimens.

This study describes the computational approach and presents validation of copy number assessment in a comprehensive, clinical grade, NGS-based cancer gene test. The observed accuracy for focal amplifications and homozygous deletions, coupled with the ability to interrogate all classes of potentially actionable alterations, suggests that this type of testing can become a routine component of cancer patient care.

Example 2: A Computational Method for Somatic vs. Germline Variant Status Determination from Targeted Next-Generation Sequencing of Clinical Cancer Specimens without a Matched Normal Control Next-generation sequencing (NGS) of cancer specimens is increasingly important to clinical oncology, as the number of therapies targeting specific genomic alterations grows. A CLIA-certified, CAP-accredited NGS-based test has been developed and deployed that interrogates the entire coding sequence of 236 selected cancer genes from minimal (≥50 ng) DNA from FFPE tissue. Deep, uniform coverage and customized algorithms permit accurate identification of all classes of genomic alterations. However, a key practical constraint in genomic testing in oncology is the limited availability of matching normal specimens, restricting the interpretation of any novel variants identified which are either private germline polymorphisms or somatic alterations. An approach to assessing somatic vs. germline status of genomic alterations without a patient matched normal, as well as determining variant zygosity and LOH, is described herein.

First, a CGH-like log-ratio profile of the sample is obtained by normalizing the coverage obtained at all exons and >3,500 genome-wide SNPs against a process-matched normal control. This profile is segmented and interpreted using allele frequencies of sequenced SNPs to estimate tumor purity (p) and copy number (C) at each segment. Fitting is performed using Gibbs sampling, assigning total copy number and minor allele count to all segments. Given a list of variants with unknown somatic/germline/zygosity status, the copy number and minor allele count (M) of the segment local to each variant is obtained. Allele frequencies f of variants of interest are interpreted using equation $$f = \frac{pM + g(1-p)}{pC + 2(1-p)},$$

where we compute the value of g. A germline variant has g=1, a somatic variant has a g=0, and a sub-clonal somatic variant has g<0. Statistical significance is assessed relative to read depth and to local variability in allele frequency estimates. Following determination of g, zygosity is determined from M and C: tumor homozygous deletion has C=M=0, tumor LOH has C=M≠0, heterozygous tumor has C≠M, and variant is absent from tumor if C≠0 and M=0.

As proof-of-principle, the approach was applied to 74 triple-negative breast cancer (TNBC) specimens from Instituto Nacional de Enfermedades Neoplásicas in Lima, Perú. 4 genes most frequently altered in the dataset were selected for analysis: TP53, BRCA1, BRCA2, and PIK3CA. As expected, 47/49 (96%) of TP53 variants were predicted somatic, with clear evidence of second copy tumor suppressor loss through LOH for 43/49 (88%). 8/8 (100%) PIK3CA variants were also predicted somatic, and 6/8 heterozygous, consistent with the PIK3CA's established role as an oncogene. In contrast, 12/18 (67%) of BRCA1/2 variants were germline, consistent with the established role for inherited BRCA1/2 variation and somatic alterations in TNBC.

This work describes a computational method based on interpretation of variant allele frequencies for determining the somatic/germline/LOH status of genomic alterations in clinical cancer specimens without a matched normal control. The method supports functional prioritization and interpretation of novel alterations discovered on routine testing and enables indication for additional diagnostic workup if predicted germline risk variants are found. When coupled with the accurate assessment of all classes of known cancer genomic alterations offered by deep NGS testing, this further informs clinical decision making and expands treatment choices for cancer patients.

Example 3: Analysis of Tumor Sample A

Inputs SCI and SAFI were acquired as described herein. Fitting a genome-wide copy number model to SCI and SAFI inputs yielded a tumor purity of 40%, with the local region around TP53 gene showing C=2, M=2. VAFI input of TP53 V157F variant has an allele frequency (AF) of 40%. Applying the equations, a value for g, g=0.01, was obtained, given the purity, C, and M from the previous step. Thus, it was concluded that this TP53 V157F is a somatic variant that is homozygous (2 of 2 copies) in the tumor.

Example 4: Analysis of Tumor Sample B

Inputs SCI and SAFI were acquired as described herein. Fitting a genome-wide copy number model to SCI and SAFI inputs yielded a tumor purity of 40%, with the local region around BRCA2 gene showing C=4, M=2. VAFI input of BRCA2 V1229I variant has an AF of 51%. Applying the equations, a value for g, g=1.05, was obtained, given the purity, C, and M from the step above. Thus, it was concluded this BRCA2 V1229I is a germline variant that is heterozygous (2 of 4 copies) in the tumor.

Example 5: Analysis of Tumor Sample C

Inputs SCI and SAFI were acquired as described herein. Fitting a genome-wide model copy number model to SCI and SAFI inputs yielded a tumor purity of 50%, with the local region around PIK3CA gene showing C=2, M=1. VAFI input of PIK3CA H419_P421>T variant has an AF of 13%. Applying the equations, obtained a value for g, g=−0.48, given the purity, C, and M from the previous step. This allele frequency of 13% is well below an expectation of AF=25% for a fully clonal somatic variant, and an AF of 50% for a germline variant. Thus, it was concluded that this PIK3CA H419_P421>T is a sub-clonal somatic variant that is heterozygous (1 of 2 copies) in the tumor.

Example 6: Analysis of Tumor Sample D

Figure 2:
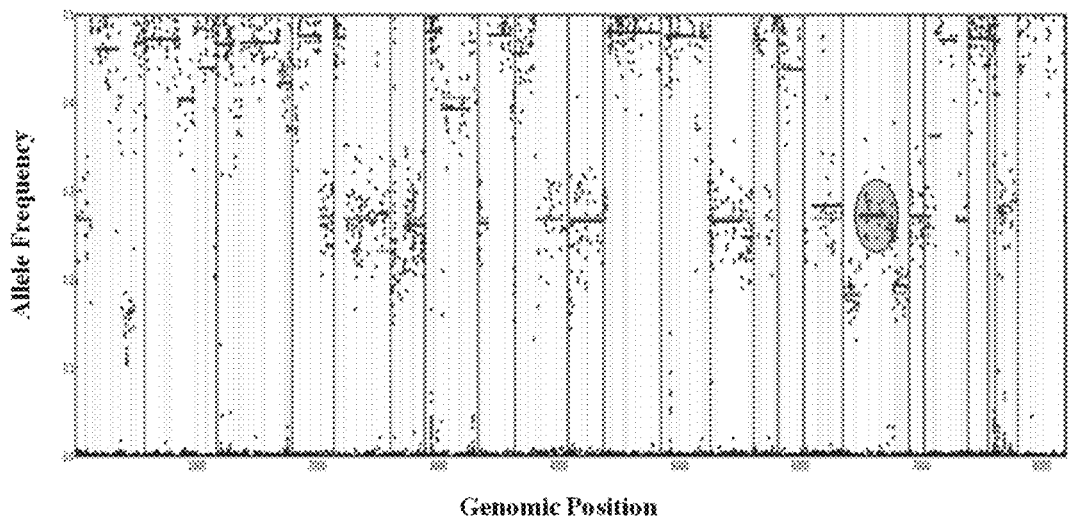
FIG. 2 depicts an exemplary germline SNP allele frequency profile of sample to acquire Input SAFI. The region that encompasses BRCA1 gene is circled.

Inputs SCI and SAFI were acquired as described herein. The CGH-like log-ratio profile used to acquire SCI is shown in FIG. 1. As shown in FIG. 1, the total local copy number for BRCA1 is 2. The germline SNP allele frequency profile used to acquire SAFI is shown in FIG. 2. As shown in FIG. 2, the allele frequency of nearby SNPs (26% or 74%) implies the number of allelic copy for BRCA1 is 0 or 2 copies. Fitting a genome-wide copy number model to SCI and SAFI inputs yielded a tumor purity of 46%, with the local region around BRCA1 gene showing C=2, M=2. VAFI input of BRCA1 I600fs*7 variant has an AF of 42%. Applying the equations, obtained a value for g, g=0, given the purity, C, and M from the previous step. Thus, it was concluded that this BRCA1 I600fs*7 variant is a somatic variant that is homozygous (2 of 2 copies) in the tumor.

Figure 9:
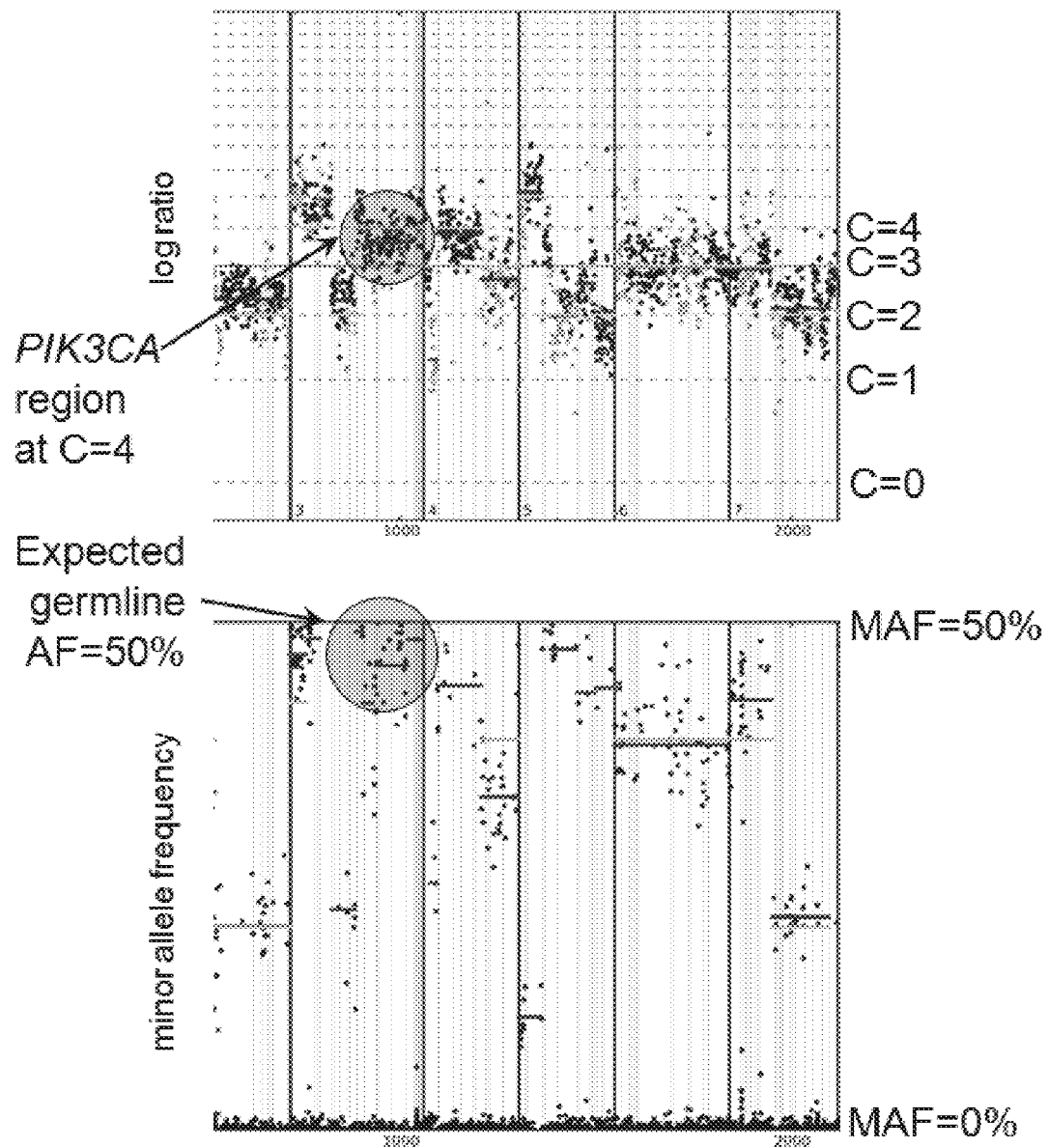
FIG. 9 depicts a CGH-like log-ratio profile of sample for determination of somatic/germline status and zygosity for PIK3CA H1047R variant.

Example 7: Known Oncogenic Driver Mutation Predicted as Somatic and Heterozygous The candidate mutation tested in this Example is PIK3CA H1047R. As shown in FIG. 9, a genome-wide copy number model indicated that the tumor has 4 copies of PIK3CA, with 2 variant alleles. The genomic segment containing PIK3CA is not under LOH in the tumor. PIK3CA H1047R variant has an allele frequency (AF) of 36%, which is significantly below threshold of a germline variant (expected AF=50%, FIG. 9) but matches a full clonal somatic mutation (expected AF=38%). Thus, it was concluded that this PIK3CA H1047R mutation is somatic and heterozygous in tumor.

Example 8: Known Tumor Suppressor Mutation Predicted as Germline with LOH

Figure 10:
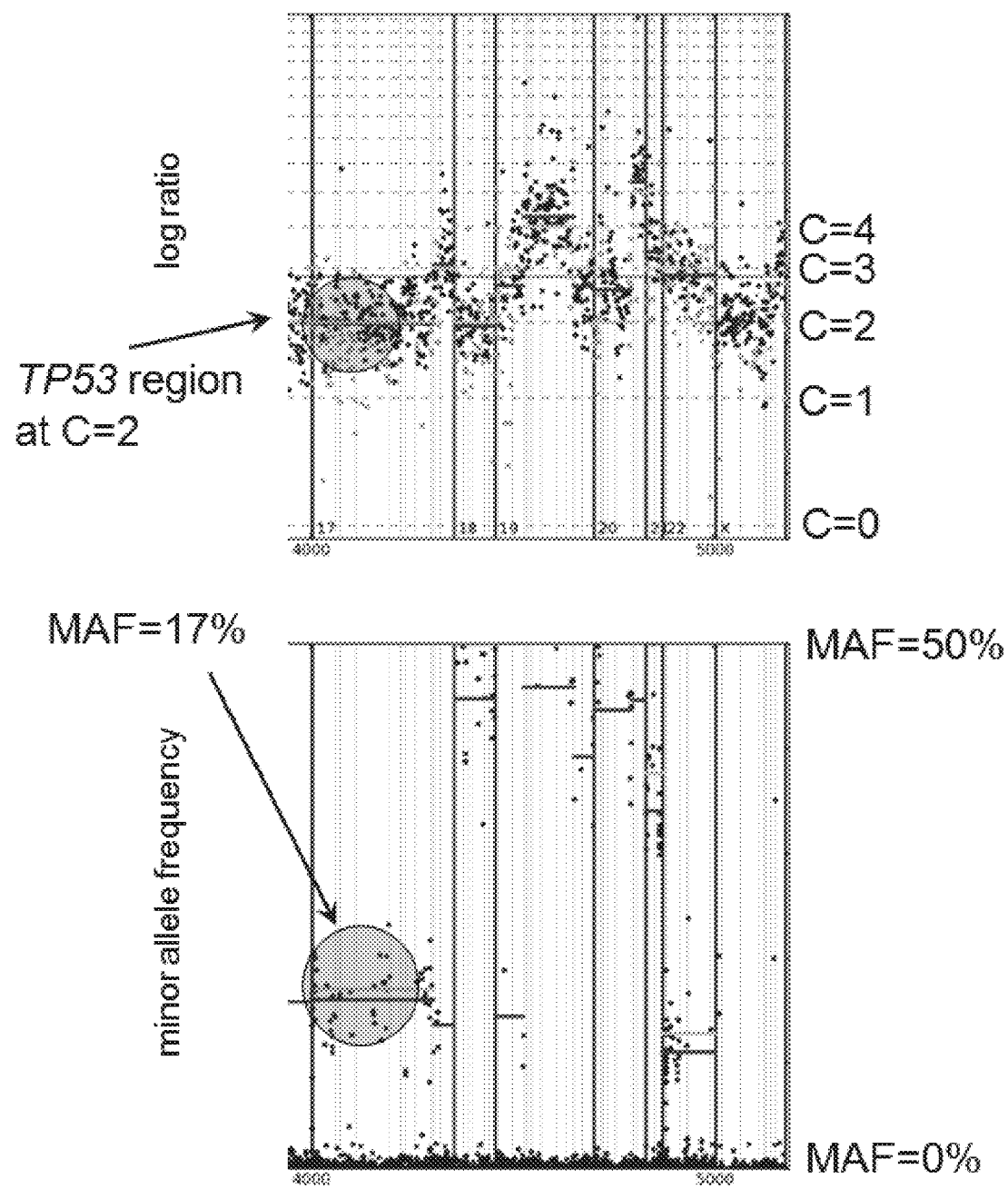
FIG. 10 depicts a CGH-like log-ratio profile of sample for determination of somatic/germline status and zygosity for TP53 G356R variant.

The candidate mutation tested in this Example is TP53 G356R. As shown in FIG. 10, a genome-wide copy number model indicated that the tumor has 2 copies of TP53, with 2 variant alleles. The genomic segment containing TP53 is under LOH in the tumor. TP53 G356R variant has an allele frequency (AF) of 85%, which is significantly above threshold of a somatic variant (expected AF=65%) but matches a germline mutation (expected AF=83%/MAF=17%, FIG. 10). Thus, it was concluded that this TP53 G356R mutation is germline and homozygous in tumor.

Figure 11:
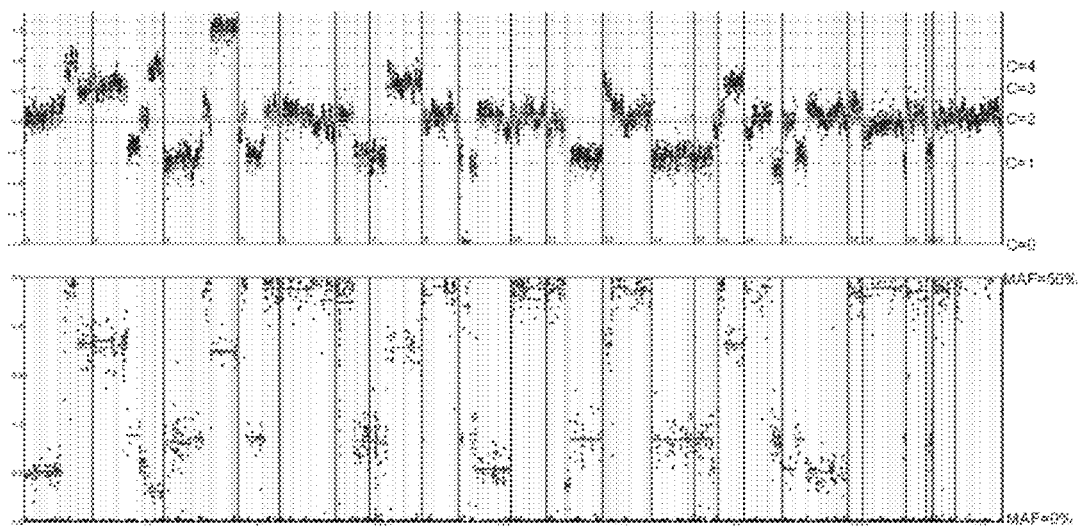
FIG. 11 depicts an exemplary CGH-like log-ratio profile of sample.

Example 9: Genome-Wide Copy Number Model Integrated with Variant Somatic vs Germline Status FIG. 11 depicts a CGH-like log-ratio profile of sample for establishing an exemplary genome-wide copy number model. Selected chromosomes are annotated with respect to copy number, zygosity, and somatic/germline status, as shown in Table 4.

TABLE 4

Genome-wide copy number model with select chromosomes annotated

| chr | start (Mb) | end (Mb) | CN | LOH | chromosome arm level gains and LOH | Status of short variant |
|---|---|---|---|---|---|---|
| chr1 | 1 | 120 | 2 | LOHx | 1p_LOHx | |
| chr3 | 1 | 90 | 1 | LOH1 | 3p_LOH1 | |
| chr3 | 130 | 198 | 6 | none | 3q_gain | |
| chr5 | 1 | 180 | 2 | none | | |
| chr8 | 1 | 146 | 2 | none | | |
| chr13 | 1 | 115 | 1 | LOH1 | chr13_LOH1 | BRCA2 D651N somatic and homozygous |
| chr17 | 1 | 8 | 1 | LOH1 | 17p_LOH1 | TP53 R282W somatic and homozygous |
| chr21 | 31 | 48 | 1 | LOH1 | | |

As indicated in FIG. 11 and Table 4, p-arm of chromosome 1 is under copy-neutral LOH (LOHx), while the entire chromosome 13 is under copy-loss LOH (LOH1). Somatic status of certain functional mutations is also reported in Table 4.

Example 10: Method Validation, Performance Evaluation and Impact Assessment of Stromal Admixture A key constraint in genomic testing in oncology is that matched normal specimens are not commonly obtained in clinical practice. Thus, while most clinically relevant genomic alterations have been previously characterized and do not require normal tissue for interpretation, the use of novel variants whose somatic status is unknown is limited. This example describes a approach to predicting somatic vs. germline status of genomic alterations from tumor tissue alone in a CLIA-certified, NGS-based test that interrogates all exons of 236 cancer-related genes.

For each sample, a "CGH"-like aneuploidy profile was obtained by normalizing against a process-matched control. This profile is segmented and modeled using allele frequencies at >3,500 SNPs to estimate the genome-wide tumor purity (p), copy number (C), and minor allele count (M) at each segment. Variant allele frequency is expected to differ based on somatic status:

$$f_{germline} = \frac{pM + 1 - p}{pC + 2(1-p)}$$

vs.

$$f_{somatic} = \frac{pM}{pC + 2(1-p)}.$$

For variants of unknown status, measured allele frequency is compared to expectation, and a prediction is made with statistical confidence assessed based on read depth and local variability of SNP measurements in each segment.

To validate the method, specimens from 30 lung and colon cancer patients were examined by sequencing the primary tumor, the metastatic tumor, and a matched-normal control. A total of 305 unique variants with known somatic status were assessed.

Next, to evaluate performance broadly, predictions for 17 somatic "hotspot" mutations (e.g. KRAS G12, PIK3CA H1047, BRAF V600E) and 20 common germline SNPs in 2,578 clinical cancer specimens were examined.

Further, to assess the impact of stromal admixture, three cell lines (HCC-1937, HCC-1954, NCI-H1395) which were experimentally titrated with their matched normal to 6 different levels (10% to 75%) were examined.

Overall, predictions could be made in about 85% of cases, with 96% of known somatic variants and 98% of known germline variants predicted correctly, as demonstrated in Table 5 below.

TABLE 5

Summary of results

| Validation study | Call rate | Somatic variants predicted correctly | Germline variants predicted correctly |
| --- | --- | --- | --- |
| 30 matched-normal samples | 84% (479/567) | 95% (311/326) | 99% (151/153) |
| 2,578 clinical samples at common somatic and germline variants | 85% (4771/5583) | 96% (2556/2665) | 98% (2062/2106) |
| 3 cell lines with varying proportions of tumor-normal admixture | 83% (184/222) | 97% (60/62) | 97% (118/122) |

This computational method leverages deep next-generation sequencing of clinical cancer specimens to predict variant somatic status without a matched-normal control. Accuracy of the method is >95%, demonstrated using three independent validation approaches. The analytic framework also assesses tumor LOH status of identified variants, and the sub-clonality of somatic mutations. It supports functional prioritization and interpretation of alterations discovered on routine testing and can indicate additional work-up if germline risk variants are found.

Example 11: Characterization Model

According to one embodiment, a characterization model can be captured and tracked over time. For example, the system can be configured to analyze and store characterization information on multiple tissue samples taken from a subject. The characterization model developed over time provides information on changes to the characterization model (including e.g., variant type, zygosity, etc.). The system can analyze the characterization model to identify relationships between different variants (e.g., tumors) based, for example, on similarity in characterization models. In some implementations, the system can identify related variants in different tumors, different patients, etc.

According to another embodiment, a characterization model can include treatment information. The system can identify related treatment options responsive to similarity in characterization models and any respective treatments. Once related treatment options are identified, the system can present related treatment in user interface displays, in a report generated by the system, etc.

Other embodiments are described within the following claims.

What is claimed is:

1. A method of characterizing a variant in a tumor sample from a subject as being a somatic or germline event, the method comprising:
  a) sequencing each of a plurality of selected subgenomic intervals, each of a plurality of selected germline SNPs, and a variant, wherein the average sequence coverage prior to normalization is at least about 250×;
  b) acquiring:
    i) a sequence coverage input (SCI), which comprises, for each of the plurality of selected subgenomic intervals, a value for normalized sequence coverage at the selected subgenomic intervals, wherein SCI comprises a comparison of the number of reads for a subgenomic interval with the number of reads for a process-matched control;
    ii) an SNP allele frequency input (SAFI), which comprises, for each of the plurality of selected germline SNPs, a value for a minor allele frequency in the tumor sample; and
    iii) for said variant being characterized, a variant allele frequency input (VAFI), which comprises the allele frequency for said variant in the tumor sample;
  c) acquiring values, as a function of SCI and SAFI, for:
    a genomic segment total copy number (C) for each of a plurality of genomic segments;
    a genomic segment minor allele copy number (M) for each of the plurality of genomic segments; and
    sample purity (p),
  wherein SCI, SAFI, C, M, and p are related to one another by the following:

$$r_{ij} \sim N\left(\log_2 \frac{p*C_i + (1-p)*2}{p*(\sum_i l_i c_i)/\sum_i l_i + (1-p)*2}, \sigma_{ri}\right), \text{ and}$$

$$fik \sim N\left(\frac{p*Mi + (1-p)*1}{p*Ci + (1-p)*2}, \sigma fi\right),$$

when SCI and SAFI are notated as $r_{ij}$ and $f_{ik}$, respectively; and where $r_{ij}$ is the log ratio (LR) of subgenomic interval j within a genomic segment ($S_i$), $C_i$ is the total copy number (C) of $S_i$, $l_i$ is the length of $S_i$, fik is the minor allele frequency of SNP k within $S_i$, $M_i$ is the copy number of a minor allele (M) at $S_i$, and $\sigma_{ri}$ and $\sigma_{fi}$ are noise parameters; and d) acquiring a value for mutation type, g, for which is indicative of the variant, being somatic, a subclonal somatic variant, germline, or not-distinguishable, wherein g, VAFI, p, C, and M are related to one another by the following:

$$VAFI = \frac{pM + g(1-p)}{pC + 2(1-p)}.$$

2. The method of claim 1, wherein
a value of g that is 0, or close to 0, indicates that the variant is a somatic variant;
a value of g that is 1, or close to 1, indicates that the variant is a germline variant;
a value of g that is less than 1 but more than 0, indicates an indistinguishable result; and
a value of g that is significantly less than 0, indicates that the variant is a subclonal somatic variant.

3. The method of claim 1, wherein the sample purity (p) is a global purity value.

4. The method of claim 1, wherein:
a value of M equal to 0 and not equal to C is indicative of absence of the variant;
a non-zero value of M equal to C is indicative of homozygosity of the variant;
a value of M equal to 0 and equal to C is indicative of homozygous deletion of the variant; and
a non-zero value of M not equal to C is indicative of heterozygosity of the variant.

5. The method of claim 1, wherein the plurality of selected subgenomic intervals comprise an exon.

6. The method of claim 1, wherein the variant is positively associated with the type of tumor present in the subject.

7. The method of claim 1, further comprising acquiring an indication of the zygosity of the variant in the tumor sample.

8. The method of claim 1, wherein the value for mutation type, g, is acquired without the use of a subject-matched normal control.

9. The method of claim 1, wherein the average sequence coverage prior to normalization is at least about 500×.

10. A system for characterizing a variant in a tumor sample as being a somatic or germline event from a subject, the system comprising:
at least one processor operatively connected to a memory, wherein the at least one processor when executing is configured to:
a) acquire:
i) a sequence coverage input (SCI), which comprises, for each of a plurality of selected subgenomic intervals, a value for sequence coverage at the selected subgenomic intervals, wherein SCI comprises a comparison of the number of reads for a subgenomic interval with the number of reads for a process-matched control, and wherein each of the plurality of selected subgenomic intervals is sequenced and the average sequence coverage prior to normalization is at least about 250×, and;
ii) an SNP allele frequency input (SAFI), which comprises, for each of a plurality of selected germline SNPs, a value for a minor allele frequency in the tumor sample, and wherein each of the plurality of selected germline SNPs is sequenced and the average sequence coverage prior to normalization is at least about 250×; and
iii) a variant allele frequency input (VAFI), which comprises the allele frequency for said variant being characterized in the tumor sample, wherein the variant is sequenced and the average sequence coverage prior to normalization is at least about 250×;
b) acquire values, determined as a function of SCI and SAFI, for:
a genomic segment total copy number (C) for each of a plurality of genomic segments;
a genomic segment minor allele copy number (M) for each of the plurality of genomic segments; and
sample purity (p),
wherein SCI, SAFI, C, M, and p are related to one another by the following:

$$r_{ij} \sim N\left(\log_2 \frac{p*C_i + (1-p)*2}{p*(\sum_i l_i c_i)/\sum_i l_i + (1-p)*2}, \sigma_{ri}\right), \text{ and}$$

$$fik \sim N\left(\frac{p*Mi + (1-p)*1}{p*Ci + (1-p)*2}, \sigma fi\right),$$

when SCI and SAFI are noted as $r_{ij}$ and $f_{ik}$, respectively; and where $r_{ij}$ is the log ratio (LR) of subgenomic interval j within a genomic segment ($S_i$), $C_i$ is the total copy number (C) of $S_i$, $l_i$ is the length of $S_i$, fik is the minor allele frequency of SNP k within $S_i$, $M_i$ is the copy number of a minor allele (M) at $S_i$, and $\sigma_{ri}$ and $\sigma_{fi}$ are noise parameters; and c) calculate a value for mutation type, g, which is indicative of the variant being somatic, germline, subclonal somatic, or not-distinguishable, wherein the at least one processor when executing is configured to calculate the value for mutation type, g, wherein g, VAFI, p, C, and M are related to one another by the following:

$$VAFI = \frac{pM + g(1-p)}{pC + 2(1-p)}.$$

11. The system of claim 10, wherein the at least one processor when executing is configured to further calculate an indication of the zygosity of the variant in the tumor sample.

12. The system of claim 10, wherein the at least one processor when executing is configured to classify the type of variant based on at least one of:
for the g value sufficiently close to 0, classify the variant as a somatic variant;
for the g value approximately equal to 1, or higher, classify the variant as a germline variant;

for the g value between 0 and 1, evaluate the g value to determine that it is not close to either the somatic classification value or the germline classification value, and classify the variant as indistinguishable; and for the g value less than 0, classify the variant as a subclonal somatic variant.

13. The system of claim 10, wherein the at least one processor when executing is configured to determine the sample purity (p) as a global purity value.

14. The system of claim 10, wherein the at least one processor when executing is configured to classify the variant according to:

a value of M equal to 0 and not equal to C indicates an absence of the variant;

a non-zero value of M equal to C indicates a homozygosity of the variant;

a value of M equal to 0 and equal to C indicates a homozygous deletion of the variant; and a non-zero value of M not equal to C indicates a heterozygosity of the variant.

15. The system of claim 10, wherein the at least one processor when executing is configured to generate a user interface.

16. The system of claim 15, wherein the user interface is configured to accept as input any one or more of:

a sequence coverage input (SCI), which comprises, for each of a plurality of selected subgenomic intervals, a value for sequence coverage at the selected subgenomic intervals;

an SNP allele frequency input (SAFI), which comprises, for each of a plurality of selected germline SNPs, a value for the allele frequency in the tumor sample;

a variant allele frequency input (VAFI), which comprises the allele frequency for said variant in the tumor sample;

a genomic segment total copy number (C) for each of a plurality of genomic segments;

a genomic segment minor allele copy number (M) for each of the plurality of genomic segments; and sample purity (p), and responsive to the user interface input the system characterizes the variant.

17. The system of claim 10, wherein the value for mutation type, g, is calculated without the use of a subject-matched normal control.

18. The system of claim 10, wherein each of the plurality of selected subgenomic intervals is sequenced and the average sequence coverage prior to normalization is at least about 500×.

19. The system of claim 10, wherein each of the plurality of selected germline SNPs is sequenced and the average sequence coverage prior to normalization is at least about 500×.

20. The system of claim 10, wherein the variant is sequenced and the average sequence coverage prior to normalization is at least about 500×.

21. The method of claim 1, wherein the SCI is the log ratio of the number of sequencing reads for the subgenomic interval in the tumor sample and the number of sequencing reads for that subgenomic interval in the process-matched control.

22. The system of claim 10, wherein the SCI is the log ratio of the number of sequencing reads for the subgenomic interval in the tumor sample and the number of sequencing reads for that subgenomic interval in the process-matched control.

* * * * *